(12) United States Patent
Ohlmeyer et al.

(10) Patent No.: US 9,796,717 B2
(45) Date of Patent: Oct. 24, 2017

(54) TRICYCLIC HETEROCYCLES AS ANTICANCER AGENTS

(71) Applicant: ICAHN SCHOOL OF MEDICINE AT MOUNT SINAI, New York, NY (US)

(72) Inventors: Michael Ohlmeyer, Plainsboro, NJ (US); David Kastrinsky, Fair Lawn, NJ (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 14/768,632

(22) PCT Filed: Feb. 19, 2014

(86) PCT No.: PCT/US2014/017127
§ 371 (c)(1),
(2) Date: Aug. 18, 2015

(87) PCT Pub. No.: WO2014/130534
PCT Pub. Date: Aug. 28, 2014

(65) Prior Publication Data
US 2015/0376191 A1    Dec. 31, 2015

Related U.S. Application Data

(60) Provisional application No. 61/766,387, filed on Feb. 19, 2013.

(51) Int. Cl.
| | | |
|---|---|---|
| A61K 31/4353 | (2006.01) | |
| C07D 487/04 | (2006.01) | |
| A61K 31/517 | (2006.01) | |
| C07D 333/80 | (2006.01) | |
| C07D 471/04 | (2006.01) | |
| A61K 31/5377 | (2006.01) | |
| A61K 31/55 | (2006.01) | |

(52) U.S. Cl.
CPC .......... C07D 487/04 (2013.01); A61K 31/517 (2013.01); A61K 31/5377 (2013.01); A61K 31/55 (2013.01); C07D 333/80 (2013.01); C07D 471/04 (2013.01)

(58) Field of Classification Search
CPC .................................................... C07D 487/04
See application file for complete search history.

(56) References Cited

U.S. PATENT DOCUMENTS

| | | | |
|---|---|---|---|
| 4,634,766 A | 1/1987 | Atkinson et al. | |
| 4,668,671 A | 5/1987 | Gribble et al. | |
| 4,882,351 A | 11/1989 | Oshima et al. | |
| 6,583,138 B1 | 6/2003 | Miyamoto et al. | |
| 9,540,358 B2 | 1/2017 | Ohlmeyer et al. | |
| 2002/0103189 A1 | 8/2002 | Miyamoto et al. | |
| 2008/0275023 A1 | 11/2008 | Guidi et al. | |
| 2017/0015625 A1 | 1/2017 | Ohlmeyer et al. | |
| 2017/0015630 A1 | 1/2017 | Ohlmeyer et al. | |

FOREIGN PATENT DOCUMENTS

| | | |
|---|---|---|
| CN | 102942562 A | 2/2013 |
| EP | 0679641 A1 | 11/1995 |
| EP | 0881220 A1 | 12/1998 |
| WO | 2004052847 A2 | 6/2004 |
| WO | 2006116157 A2 | 11/2006 |
| WO | 2006117183 A1 | 11/2006 |
| WO | 2013/025882 A2 | 2/2013 |
| WO | 2014031986 A1 | 2/2014 |
| WO | 2015138496 A1 | 9/2015 |
| WO | 2015138500 A1 | 9/2015 |

OTHER PUBLICATIONS

International Search Report for PCT/US2014/017127 dated May 20, 2014.
(Continued)

*Primary Examiner* — Brian McDowell
(74) *Attorney, Agent, or Firm* — Heslin Rothenberg Farley & Mesiti, P.C.; Philip Hansen

(57) ABSTRACT

Tricyclic chemical modulators of FOXO transcription factor proteins are disclosed. The compounds are useful to treat cancer, age-onset proteotoxicity, stress-induced depression, inflammation, and acne. The compounds are of the following and similar genera:

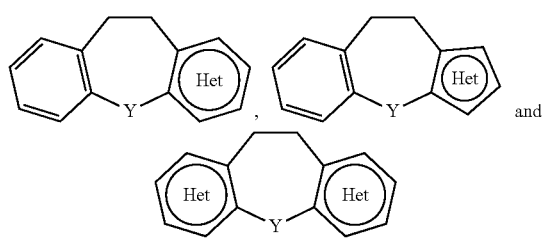

in which Het is an aromatic heterocyclic ring and Y is a point of attachment of various side chains and rings. An example of such a compound is 4-chloro-N-(3-(10,11-dihydro-5H-benzo[b]pyrido[2,3-f]azepin-5-yl)propyl)benzenesulfonamide:

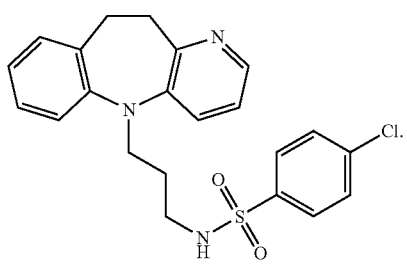

14 Claims, No Drawings

(56) References Cited

OTHER PUBLICATIONS

Motohashi, et al; "Synthesis and biological activity of N-acylphenothiazines," International Journal of Antimicrobial Agents, 2000, pp. 203-207, vol. 14.

Morak-Mlodawska, et al., Acyl and Sulfonyl Derivatives of 10-Aminoalkyl-2,7-Diazaphenothiazines#, Hetrocycles, vol. 78, No. 5, 2009.

Alfonso, et al, Synthesis of a $C_{11}$ Spiropiperdino derivative of 8-Chloro-6,11-dihydro 5H—Benzo[5,6]cyclohepta[1,2-b]pyridine, Tetrahedron Letters 39, 1998, 7661-7664.

International Search Report for PCT/US2014017127 dated Jun. 16, 2014.

Kau, et al., A chemical genetic screen identifies inhibitors of regulated nuclear export of a Forkhead transcription factor in PTEN-deficient tumor cells, Cancer Cell, XP008037524, Dec. 2003.

Jelen, et al., Synthesis of 6-Aminoalkyldiquino-1,4-Thiazines and Their Acyl and Sulfonyl Derivatives, Heterocycles, vol. 4, No. 4, XP055279565, 2008.

Pluta, et al., Anticancer activity of newly synthesized azaphenothiazines from NCI's anticancer screening bank#, Pharmaceutical Reports, 2010, 62, 319-332.

Database PubChemCompound, "N-[4-methoxy-3-(3-phenothiazin-10-ylpropylsulfamoyl)phenyl]acetamide," URL: http://pubchem.ncbi.nlm.nih.gov/search/search.cgi, 2005-2009.

Alfredsson et al., "Mass Fragmentographic Analysis of Clomipramine and Its Mono-Demethylated Metabolite in Human Plasma" Psychopharmacology, 52, 25-30 (1977).

Midgley et al., "Synthesis of [13C$_2$]-Amitriptyline, Nortriptyline and Desmethynortriptyline" Journal of Labelled Compounds and Radiopharmaceuticals, vol. XV, pp. 511-521 (1978).

Hadrich et al., "Synthesis and Characterization of Fluorescent Ligands for the Norepinephrine Transporter: Potential Neuroblastoma Imaging Agents", J. Med. Chem., 1999, (published on web Jul. 16, 1999).

Runyon et al., "Influence of Chain Length and N-Alkylation on the Selective Serotonin Receptor Ligand 9-(Aminomethyl)-9,10-dihydroanthracene", Bioorganic & Medicinal Chemistry Letters 11 (2001), 655-658.

Van Dort et al., Synthesis of [11]C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.

Ilies et al., "Protease Inhibitors: Synthesis of Bacterial Collagenase and Matrix Metalloproteinase Inhibitors Incorporating Arylsulfonylureido and 5-Dibenzo-suberenyl/suberyl Moieties", Bioorganic & Medicinal Chemistry, 11 (2003) 2227-2239.

Yang et al., "Catalytic decarboxylative alkylationof B-keto acids with sulfonamides via the cleavage of carbon-nitrogen and carbon-carbon bonds," Chemical Communications, 2011 (published on Web: Jun. 22, 2011), vol. 47, No. 29, pp. 8343-8345.

Azuine et al., "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.

Ohshima, et al., "Non-Prostanoid Thromboxane $A_2$ Receptor Antagonists with a Dibenzoxepin Ring System. 2" J. Med. Chem, 1992, 35, 3402-3413.

RN 1350122-38-1 CAS Registry.

Extended EP Search Report for EP 12823881.3 dated Mar. 3, 2015.

International Search Report for PCT/US2012/051097 dated Feb. 20, 2013.

International Search Report for PCT/US2015/019764 dated May 8, 2015.

International Search Report for PCT/US2015/019770 dated May 8, 2015.

International Search Report for PCT/US2016/050685 dated Oct. 18, 2016.

International Search Report for PCT/US2016/050688 dated Oct. 18, 2016.

International Search Report for PCT/US2016/045779 dated Sep. 30, 2016.

International Search Report for PCT/US2016/050690 dated Oct. 18, 2016.

International Search Report for PCT/US2016/050696 dated Oct. 18, 2016.

International Search Report for PCT/US2016/050692 dated Oct. 18, 2016.

O'Brien et al., "cis- and trans-Stereoselective Epoxidation of N-protected 2-Cyclohexen-1-ylamines," Organic Letters, 2003, 14(23), 6012-6015.

TRICYCLIC HETEROCYCLES AS ANTICANCER AGENTS

CROSS REFERENCE TO RELATED APPLICATIONS

This application is a national phase filing under 35 U.S.C. §371 of PCT International Application PCT/US2014/017127, filed Feb. 19, 2014, and published under PCT Article 21(2) in English as WO 2014/130534 A1 on Aug. 28, 2014. This application claims priority from U.S. provisional application 61/766,387, filed Feb. 19, 2013, the entire contents of which are incorporated herein by reference.

FIELD OF THE INVENTION

The invention relates to the use of tricyclic heterocycles, which are modulators of FOXO transcription factor proteins, to treat cancer, age-onset proteotoxicity, stress-induced, depression, inflammation, and acne.

BACKGROUND

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family, and in particular FOXO1, is controlled by cytosolic-nuclear translocation with nuclear FOXO1 exerting its actions either directly by transcriptional activation of its target genes or indirectly by interaction with other nuclear transcription factors.

The compounds described herein, which are based on tricyclic scaffolds, exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of tricyclics has now been found that induce FOXO1 transcription factor translocation to the nucleus. The compounds described herein exhibit anti-proliferative effects, and are useful in the treatment of a variety of disorders, including as a monotherapy in cancer treatment, or used in combination with other drugs to restore sensitivity to chemotherapy where resistance has developed.

In a first aspect the invention relates to compounds of formula (I):

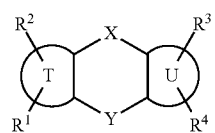

wherein:
T is a benzene ring or a five or six membered heteroaromatic ring;
U is a benzene ring or a five or six membered heteroaromatic ring;
with the proviso that at least one of T and U is other than a benzene ring;
X is selected from the group consisting of: —S—, —(CH$_2$—CH$_2$)—, and —CH=CH—;
Y is selected from the group consisting of:

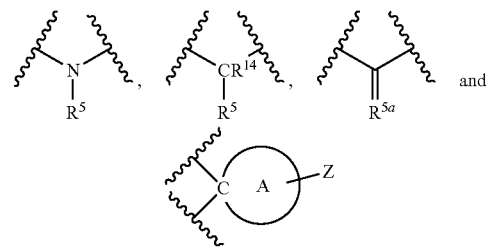

A is a three to six membered aliphatic carbocycle or heterocycle attached at Y as a spiro ring, and A may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy;
R$^1$, R$^2$, R$^3$, and R$^4$ are independently selected from the group consisting of: H, halo, —N$_3$, —NR$^6$R$^7$, (C$_1$-C$_6$)alkyl, (C$_1$-C$_6$)haloalkyl, —OR$^6$, —C(O)R$^6$, —OC(O)R$^6$, —C(O)NR$^6$R$^7$, —C(O)OR$^6$, —SR$^6$, —SO$_2$R$^6$, and —SO$_2$NR$^6$R$^7$;
R$^5$ is —(CR$^{15}$R$^{16}$)$_p$-Q$_q$-(CR$^{15}$R$^{16}$)$_{n-p}$—Z or

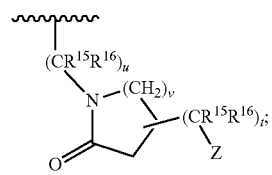

R$^{5a}$ is =CR$^{14}$(CR$^{15}$R$^{16}$)$_p$-Q$_q$-(CR$^{15}$R$^{16}$)$_{m-p}$—Z;
Q is chosen from —O—, —NR$^{14}$— and

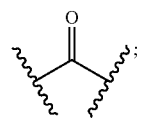 [SMILES: *C(*)=O]

each R$^6$ and R$^7$ is independently selected from the group consisting of: H and (C$_1$-C$_6$)alkyl;
R$^{14}$ is H or (C$_1$-C$_3$)alkyl;
R$^{15}$ and R$^{16}$, in each occurrence are chosen independently from H, OH, cyano, amino, (C$_1$-C$_3$)alkylamino, (C$_1$-

$C_3$)dialkylamino, ($C_1$-$C_3$)alkyl, ($C_1$-$C_3$)haloalkyl, ($C_1$-$C_3$)haloalkoxy, and ($C_1$-$C_3$)alkoxy, or, taken together, two of $R^{14}$, $R^{15}$ and $R^{16}$ may form a three to seven membered carbocycle or heterocycle wherein said three to seven membered carbocycle or heterocycle may be additionally substituted with one or two substituents chosen from OH, F, cyano, amino, ($C_1$-$C_3$) alkylamino, ($C_1$-$C_3$)dialkylamino, ($C_1$-$C_3$)alkyl, ($C_1$-$C_3$)haloalkyl, ($C_1$-$C_3$)haloalkoxy, and ($C_1$-$C_3$)alkoxy;

m is an integer from 1 to 3;
n is an integer from 2 to 4;
p is zero, 1 or 2;
q is zero or 1;
t is zero, 1 or 2;
u is zero, 1 or 2, with the proviso that when Y is

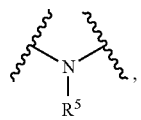

u is 2;
v is 1, 2 or 3;
Z is selected from the group consisting of: —NHSO$_2$R$^{17}$, —NHC(O)NR$^8$R$^9$, —NHC(O)OR$^8$, —S(O)$_2$NR$^8$R$^9$, substituted or unsubstituted cyclic carbamate; substituted or unsubstituted cyclic urea, cyclic imide, cyanoguanidine;

R$^8$ and R$^9$ are independently selected from H, substituted or unsubstituted ($C_1$-$C_6$)alkyl, and substituted or unsubstituted ($C_3$-$C_7$) cycloalkyl; and R$^{17}$ is chosen from phenyl and monocyclic heteroaryl, said phenyl and monocyclic heteroaryl optionally substituted with one or two substituents chosen from OH, halogen, cyano, nitro, ($C_1$-$C_3$)alkylamino, ($C_1$-$C_3$)dialkylamino, ($C_1$-$C_3$)acylamino, ($C_1$-$C_3$)alkylsulfonyl, ($C_1$-$C_3$)alkylthio, ($C_1$-$C_3$)alkyl, ($C_1$-$C_3$)haloalkyl, ($C_1$-$C_3$)haloalkoxy, and ($C_1$-$C_3$)alkoxy.

In a second aspect, the invention relates to methods and uses of the above-described compounds in medicine, particularly for the treatment of a disease chosen from: (a) cancer; (b) diabetes; (c) autoimmune disease; (d) age onset proteotoxic disease; (e) mood disorder; (f) acne vulgaris; (g) solid organ transplant rejection; (h) graft vs host disease; and (i) cardiac hypertrophy.

In a third aspect, the invention relates to pharmaceutical compositions comprising the above-described compounds.

DETAILED DESCRIPTION OF THE INVENTION

Substituents are generally defined when introduced and retain that definition throughout the specification and in all independent claims.

In a composition aspect, the invention relates to compounds of formula (I):

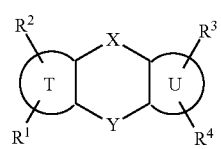

I as described above. Subgenera of the formula I include the following:

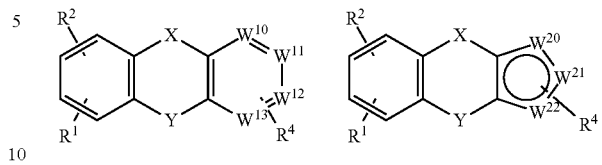

in which each of $W^{10}$, $W^{11}$, $W^{12}$ and $W^{13}$ is independently chosen from N, CH and C—R$^3$; and each of $W^{20}$, $W^{21}$ and $W^{22}$ is independently chosen from S, O, NH, CH and C—R$^3$.

In some subgenera, Z is selected from —NHSO$_2$R$^{17}$, —NHC(O)NR$^8$R$^9$, and —NHC(O)OR$^8$.

In the subgenus in which Z is —NHSO$_2$R$^{17}$, some compounds are of formula:

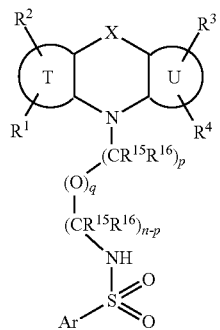

wherein Ar is a substituted or unsubstituted phenyl, thienyl, furanyl or pyrrolyl. And, in particular, they may be of formula (IA) or (IA'):

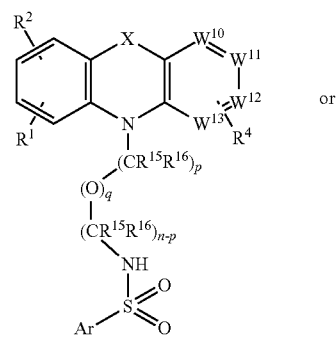

IA or

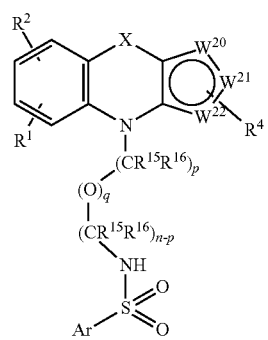

IA' in which $R^1$ and $R^4$ are independently selected from H and halo; and $R^2$ is H.

In certain embodiments, X is —CH=CH— or —CH$_2$CH$_2$—. These are represented by the formula

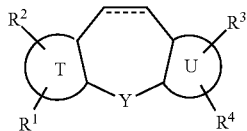

in which the dashed line is intended to represent an optional double bond. In other words, the foregoing formula represents either

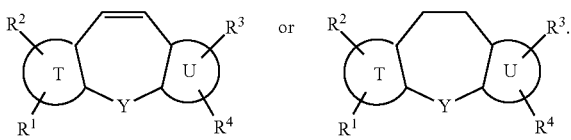

In certain embodiments p and q are both zero, $R^{15}$ is H and $R^{16}$ is chosen from H and OH. Examples of such subgenera in which Y is N include:

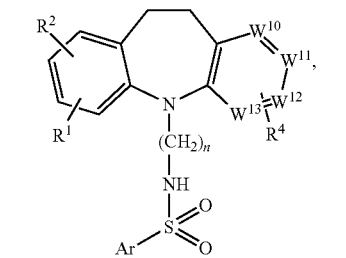

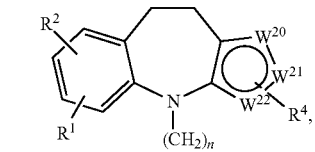

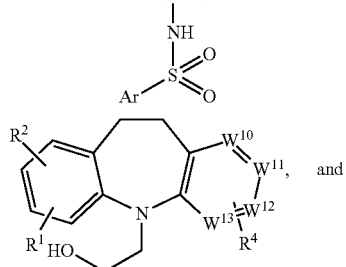

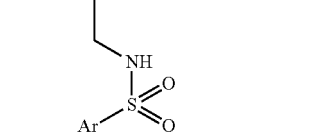

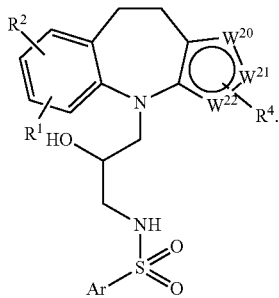

Other compounds in the genus in which Z is —NHSO$_2$R$^{17}$ and Y is N are in subgenera of formulae:

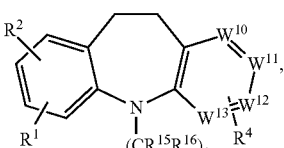

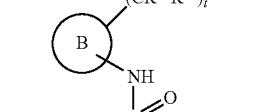

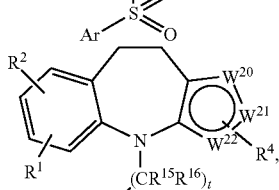

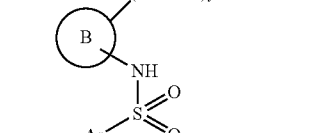

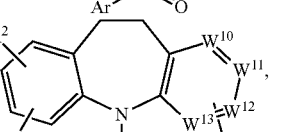

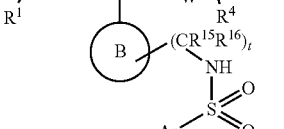

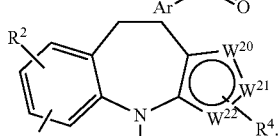

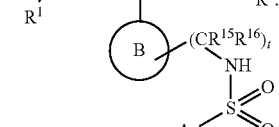

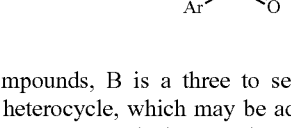

In these compounds, B is a three to seven membered carbocycle or heterocycle, which may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy. And t is zero, 1 or 2.

When Y is

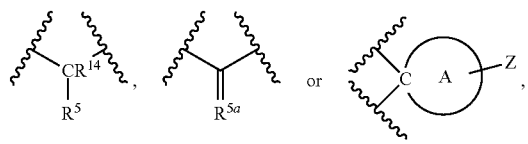

exemplary genera include:

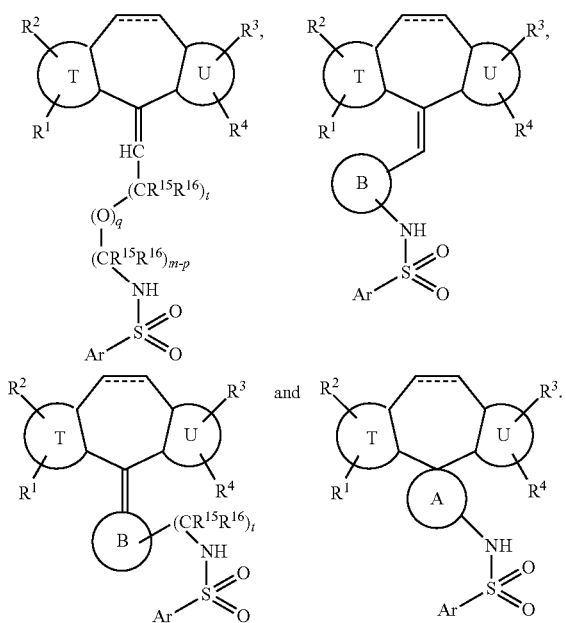

Examples of rings "A" and "B" include cyclopentyl, cyclohexyl, tetrahydrofuranyl, tetrahydropyranyl, pyrrolidinyl, piperidinyl and piperazinyl, each of which may be substituted with oxo or hydroxyl. Ar is commonly a substituted or unsubstituted phenyl, thienyl, furanyl or pyrrolyl. In these subgenera, as in others, t may be zero.

Particular embodiments of the substituent $R^5$ that contain "B" rings are, for example:

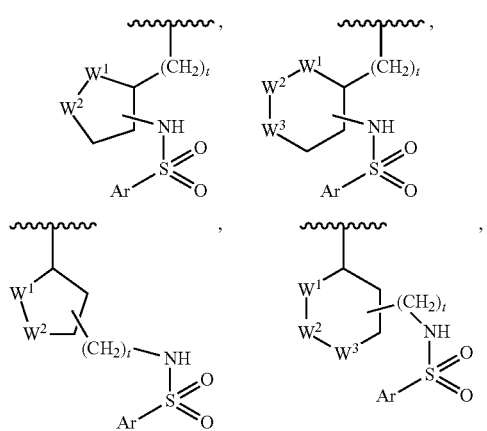

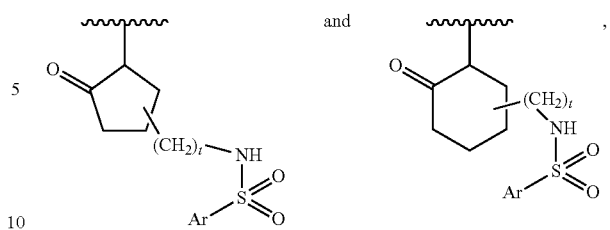

in which the wavy line indicates the point of attachment of $R^5$ to the ring node identified as "Y", which can be either N or $CR^{14}$ in the parent structure I.

Particular embodiments of the substituent $R^{5a}$ that contain "B" rings are, for example:

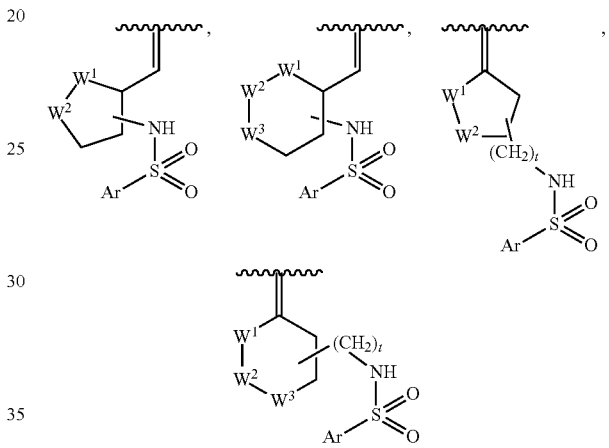

in which the wavy line indicates the point of attachment of $R^{5a}$ to the ring node identified as "Y" in the parent structure I.

Particular embodiments when Y is

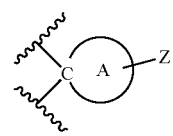

that contain "A" rings are, for example spiro[cyclopentanes], spiro[cyclohexanes], and tetrahydro spiro[furans] and spiro[pyrans]:

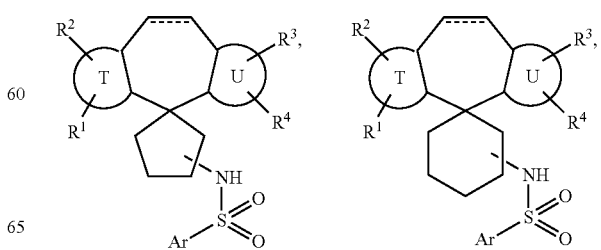

-continued

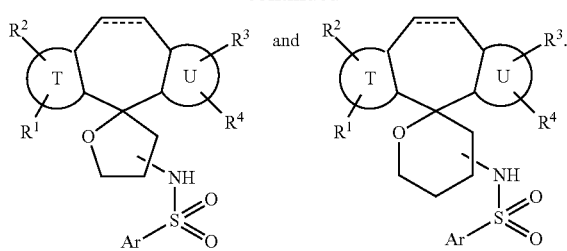

Subgenera of the foregoing are those in which one of T and U is phenyl and the other of T and U is pyridine, pyrimidine, pyrazine or pyridazine, e.g.:

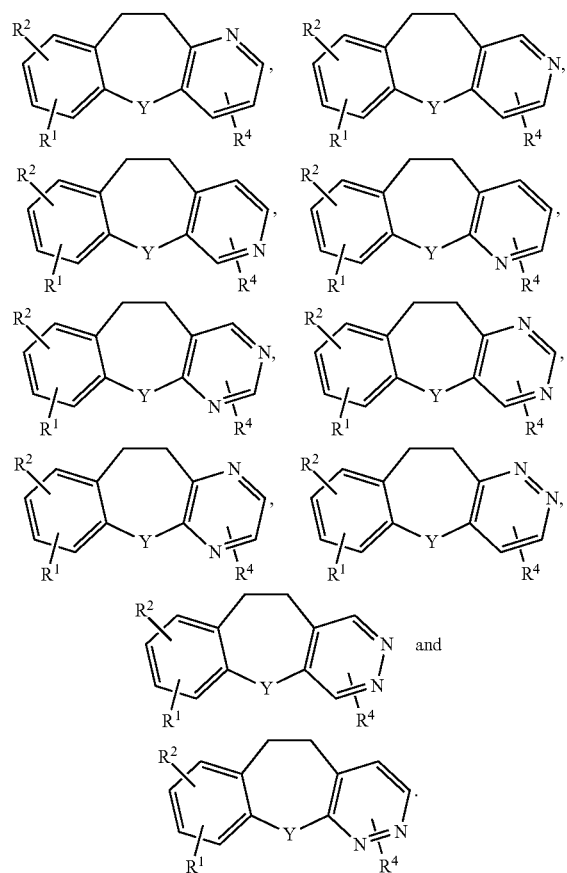

Other subgenera of the foregoing are those in which one of T and U is phenyl and the other of T and U is thiophene:

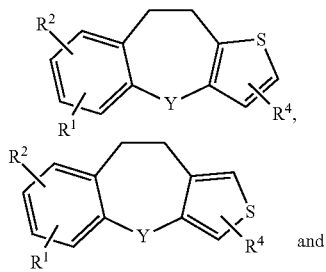

-continued

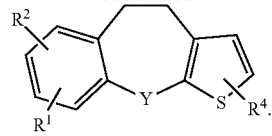

In certain embodiments, Ar is phenyl or thienyl, optionally substituted with one or two substituents chosen from methyl, halogen, cyano, nitro, trifluoromethyl, methylsulfonyl, trifluoromethoxy, and acetylamino. In compounds of the invention, Ar is restricted to monocyclic aryl and heteroaryl because, in the bicyclic examples tested, little or no activity was observed. In some of the embodiments of the invention the one or two substituents are located at positions that are not adjacent to the point of attachment of Ar to the sulfonamide. To illustrate, when Ar is thienyl, 3-chloro-2-thienyl has a halogen substituent adjacent the point of attachment, whereas 4-chloro-2-thienyl does not. In certain embodiments, Ar is phenyl, optionally substituted at the 3, 4 or 5 positions with one or two substituents chosen from methyl, halogen, cyano, trifluoromethyl and trifluoromethoxy. In embodiments in which $R^5$ is —$(CR^{15}R^{16})_p$-$Q_q$-$(CR^{15}R^{16})_{n-p}$—Z and in which p and q are zero, when $R^{15}$ and $R^{16}$ are H in all occurrences, n may be 2 or 3.

In one subgenus in which Z is chosen from —NHC(O)NR$^8$R$^9$ and —NHC(O)OR$^8$, R$^9$ is hydrogen and R$^8$ is ($C_1$-$C_6$)alkyl.

In many embodiments $R^1$ and $R^3$ are independently selected from the group consisting of H and halo and $R^2$ and $R^4$ are H.

It may be found upon examination that compounds or methods not presently excluded are not patentable to the inventors in this application. In either case, the exclusion of species and genera in applicants' claims are to be considered artifacts of patent prosecution and not reflective of the inventors' concept or description of their invention, which encompasses all species within genus I that are not in the public's possession.

As used herein, and as would be understood by the person of skill in the art, the recitation of "a compound"—unless expressly further limited—is intended to include salts of that compound. Thus, for example, the recitation "a compound of formula"

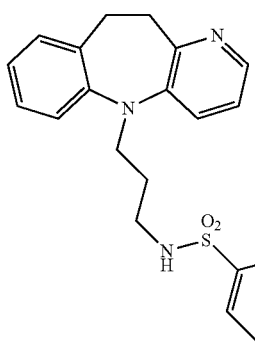

as depicted above would include salts in which the pyridine nitrogen is protonated

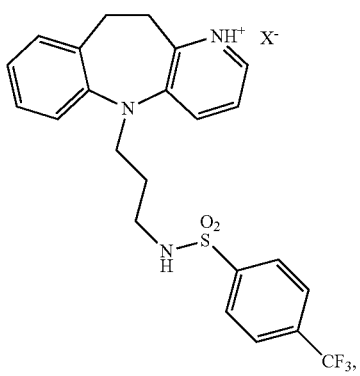

wherein X⁻ is any counterion. In a particular embodiment, the term "compound of formula I" refers to the compound or a pharmaceutically acceptable salt thereof. Unless otherwise stated, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Unless otherwise stated, all tautomeric forms of the compounds of the invention are within the scope of the invention.

Also provided herein is a pharmaceutical composition comprising a compound of formula (I), or a pharmaceutically acceptable salt form thereof, and a pharmaceutically acceptable carrier or diluent.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature.

Radioisotopes of hydrogen, carbon, phosphorous, fluorine, and chlorine include $^2$H, $^3$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Compounds that contain isotopes $^{11}$C, $^{13}$N, $^{15}$O, and $^{18}$F are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula (I), or a pharmaceutically acceptable salt form thereof. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more cancer chemotherapeutic agents. In some embodiments, the one or more cancer chemotherapeutic agents are EGFR inhibitors. For example, the chemotherapeutic agent may be erlotinib or gefitinib.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors. For example, the chemotherapeutic agent is erlotinib or gefitinib.

In some embodiments, administration of a compound of formula (I) or a pharmaceutically acceptable salt form thereof, can restore sensitivity to one or more chemotherapeutic agents in a patient wherein the patient has developed a resistance to the one or more chemotherapeutic agents.

Also provided herein is a method for treating diabetes in a patient, the method comprising administering to the patient a therapeutically effective amount of a compound of formula (I), or a pharmaceutically acceptable salt form thereof.

Further provided herein is a method for treating an autoimmune disease in a patient, the method comprising administering to the patient a therapeutically effective amount of a compound of formula (I). The autoimmune disease can be, for example, inflammatory bowel disease (IBD). Immune responses are constantly and tightly regulated and one important cellular component in maintaining self tolerance (ie prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)]. Compounds of the present invention may be used alone or in combination with conventional immunosuppressive drugs such as cyclosporine, FK506 or rapamycin and its analogs. In addition compounds of the present invention may be co-administered with histone deacetylase inhibitors (HDACi) which have been shown to enhance Treg function by maintaining Foxp3 acetylation and activity.

Aspects of the invention include methods for treatment of autoimmune disease characterized by deficiency in Treg function comprising administering a therapeutically useful amount of compound of Formula I, optionally in combination with an HDAC inhibitor. The method can also include extraction of naïve T-cells from a patient, differentiation of T-cells to Tregs ex vivo by treatment with a compound of Formula I, optionally supplemented with an HDACi, followed by administration of Tregs to patient with optional separation of compound of Formula I from Tregs prior to their administration. As stated above, autoimmune diseases that can be so treated include IBD, solid organ transplant rejection, and GvHD in allo-HCT. by treatment of donor cell inoculum with a therapeutically useful amount of compound of Formula I.

In some embodiments, the compounds can be administered to a patient to treat an autoimmune disorder, for example, Addison's disease, Amyotrophic Lateral Sclerosis, celiac disease, Crohns disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis.

In some embodiments, the compound provided herein can be used for treating a disease or disorder in a patient wherein the disease or disorder involves excessive or unregulated cellular proliferation, the method comprising administering to the patient a therapeutically effective amount of a compound of formula (I). Also provided herein is a method for treating a disease or disorder in a patient where the disease or disorder involves the dysregulation of the pi3K-AKT-FOXO signaling pathway, the method comprising administering to the patient a therapeutically effective amount of a compound of formula (I).

Further provided herein is a method for treating a disease in a patient wherein the disease is characterized by age onset proteotoxicity, the method comprising administering to the patient a therapeutically effective amount of a compound of formula (I). In some embodiments, the disease is selected from the group consisting of: Alzheimer's disease, Parkinson's disease, Huntington's disease, and amyotrophic lateral sclerosis.

The compounds provided herein may further be used in a method for treating a mood disorder in a patient, the method comprising administering to the patient a therapeutically effective amount of a compound of formula (I). In some embodiments, the mood disorder is stress induced depression.

Also provided herein is a method for treating acne vulgaris in a patient, the method comprising administering to the patient a therapeutically effective amount of a compound of formula (I).

Further provided herein is a method for treating cardiac hypertrophy in a patient, the method comprising administering to the patient a therapeutically effective amount of a compound of formula (I). In some embodiments, the cardiac hypertrophy is associated with a disease selected from hypertension, myocardial infarction, and valvular heart disease.

The compounds are described herein induce FOXO1 transcription factor translocation to the nucleus. They exhibit anti-proliferative effects, but minimal dopamine binding and are thus likely to have reduced GPCR-mediated CNS and CV side effects. These agents are useful in the treatment of a variety of disorders, including as a monotherapy in cancer treatment, or used in combination with other drugs to restore sensitivity to chemotherapy where resistance has developed.

More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula (I), or a pharmaceutically acceptable salt form thereof, to a patient, wherein a therapeutically effective amount of one or more additional cancer chemotherapeutic agents are administered to the patient. Examples of suitable chemotherapeutic agents include EGFR inhibitors such as erlotinib or gefitinib.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes upregulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

Unless otherwise specified, alkyl is intended herein to include linear, branched, or cyclic hydrocarbon structures and combinations thereof. Straight-chain alkyl groups include methyl, ethyl, n-propyl, n-butyl, n-pentyl, n-hexyl, n-heptyl, n-octyl, n-nonyl, and n-decyl and branched-chain alkyl groups include isopropyl, tert-butyl, isobutyl, sec-butyl, and neopentyl. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl, as used herein, is a subset of alkyl and includes cyclic hydrocarbon groups of from 3 to 8 carbon atoms. In some taxonomies or systems of nomenclature, e.g. IUPAC, cycloalkyl is treated as separate from alkyl, rather than as a subset. To accommodate such classifications, or to accommodate readers for whom placing straight, branched and cycloalkyls within the term alkyl is repugnant, what is here called alkyl could be referred to as "saturated hydrocarbyl" or "alkyl/cycloalkyl". Examples of cycloalkyl groups include cyclopropyl, cyclobutyl, cyclopentyl, cyclohexyl, cycloheptyl, norbornyl and the like. In certain embodiments, a straight chain or branched chain alkyl has 6 or fewer carbon atoms in its backbone (e.g., $C_{1-6}$ for straight chain, $C_{3-6}$ for branched chain). The term $C_{1-6}$ includes alkyl groups containing 1 to 6 carbon atoms. In some embodiments, cycloalkyls have from 3-8 carbon atoms in their ring structure, for example, they can have 3, 4, 5 or 6 carbons in the ring structure.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles. Carbocycles may be divided into aliphatic (i.e. non-aromatic) carbocycles and aromatic carbocycles. Aromatic carbocycles include benzene (phenyl) and naphthalene (naphthyl); aliphatic carbocycles include cycloalkyl, such as cyclopropyl, cyclobutyl, cyclopentyl, cyclohexyl, cycloheptyl, and carbocycles having unsaturation, such as cyclohexene, cyclopentene, cycloheptene, and cycloheptadiene.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. The double bonded oxygen, when referred to as a substituent itself is called "oxo".

Aryl and heteroaryl, in general, mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein with respect to the substituent Ar, aryl and heteroaryl refer to monocyclic residues.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloaliphatic or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles include pyrrolidine, pyrazole, pyrrole, indole, quinoline, isoquinoline, tetrahydroisoquinoline, benzofuran, benzodioxan, benzodioxole, tetrazole, morpholine, thiazole, pyridine, pyrazine, pyridazine, pyrimidine, thiophene, furan, oxazole, oxazoline, isoxazole, dioxane, tetrahydrofuran, tetrahydropyran and the like. It is to be noted that heteroaryl is a subset of heterocycle in which the heterocycle is aromatic. An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

As used herein, the term "optionally substituted" may be used interchangeably with "unsubstituted or substituted". The term "substituted" refers to the replacement of one or more hydrogen atoms in a specified group with a specified radical. "Oxo" may also be included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(=O)Oalkyl, respectively.

The term "halogen" means fluorine, chlorine, bromine or iodine. In one embodiment, halogen may be fluorine or chlorine.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

Compounds according to the invention can be prepared as shown in the Schemes below.

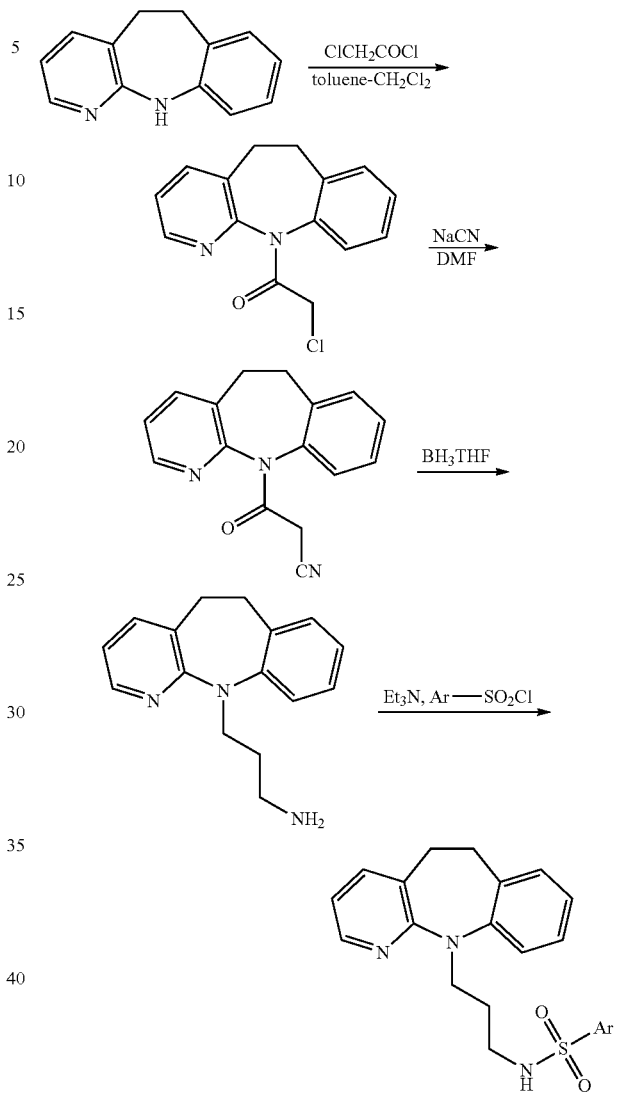

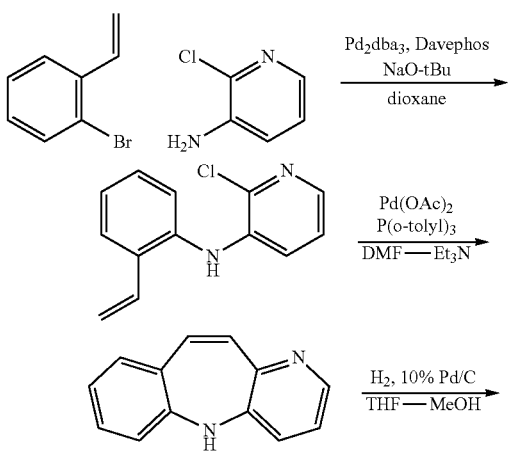

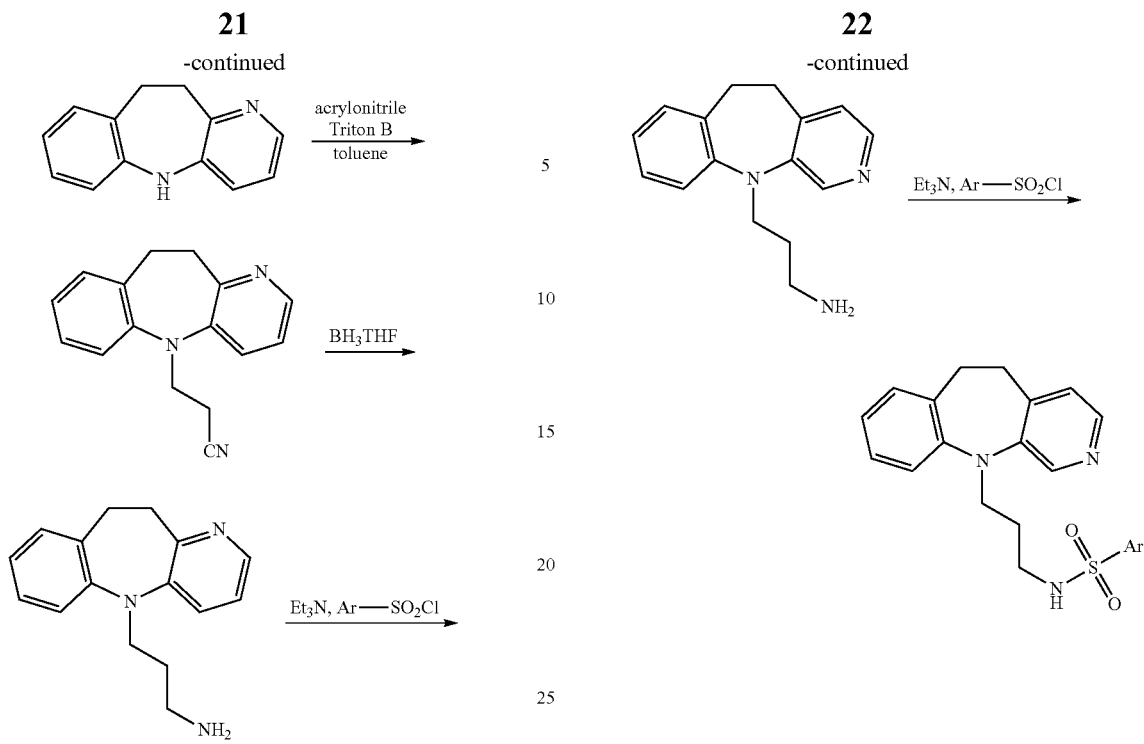
Scheme 3
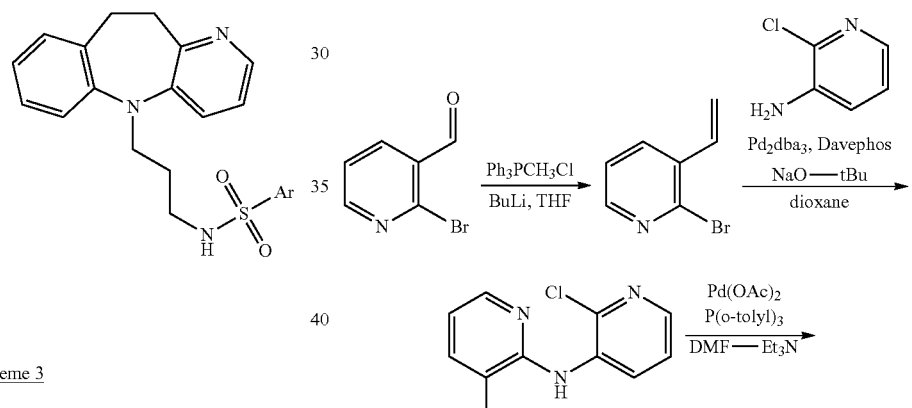
Scheme 4
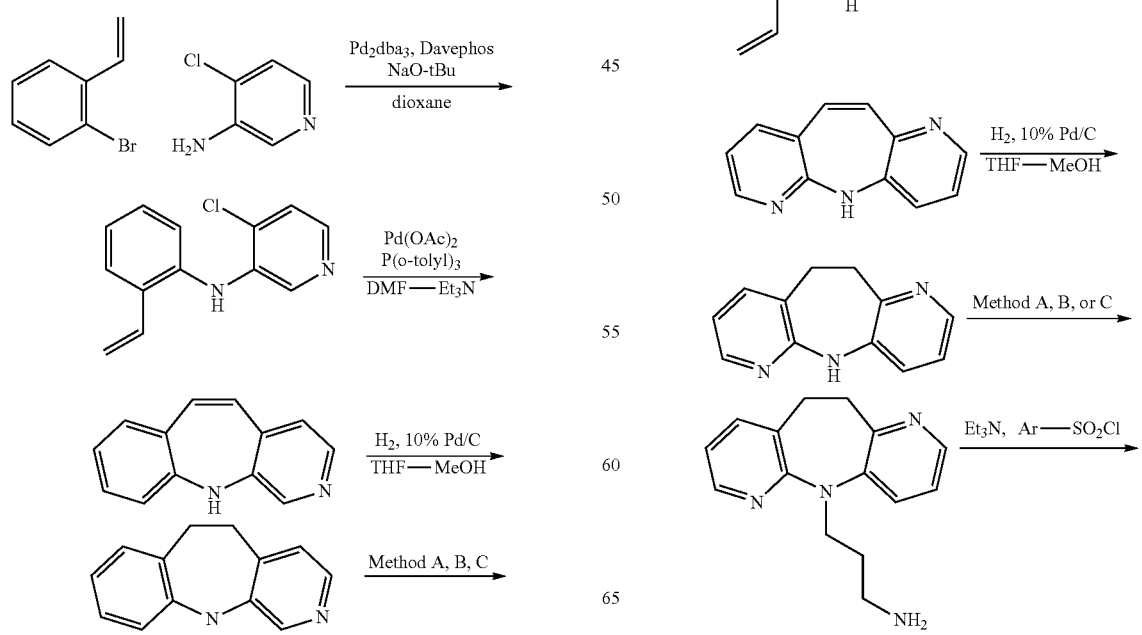

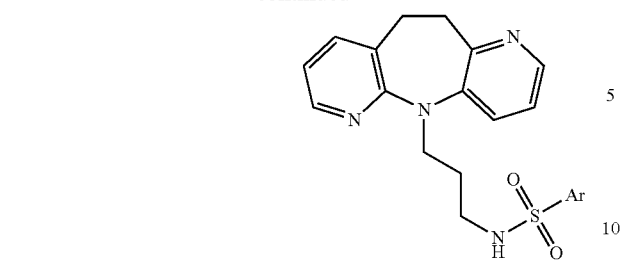
Scheme 5
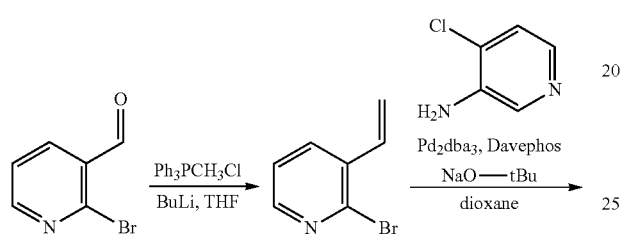
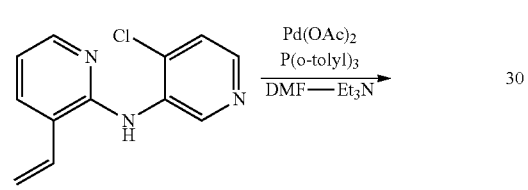
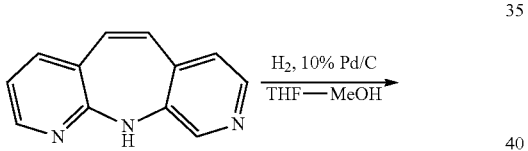
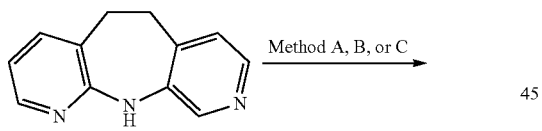
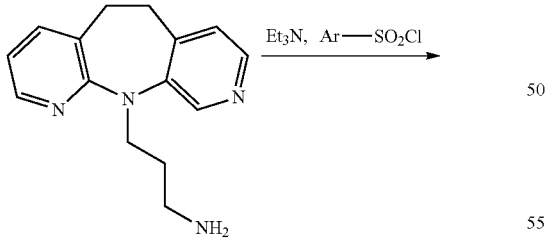
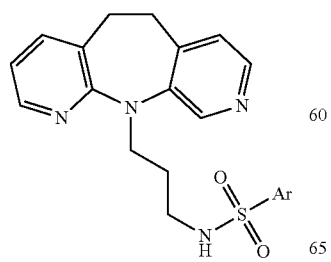
Scheme 6
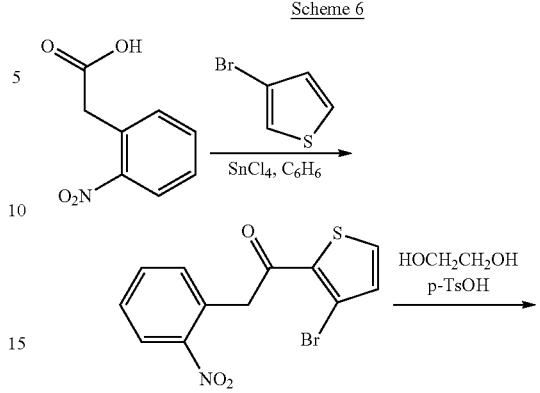
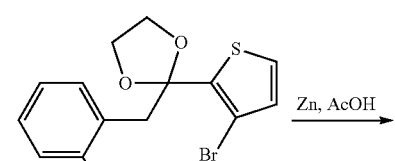
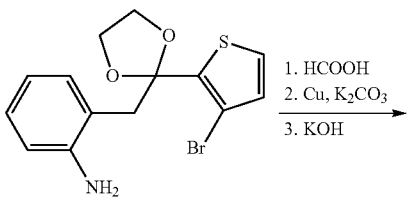
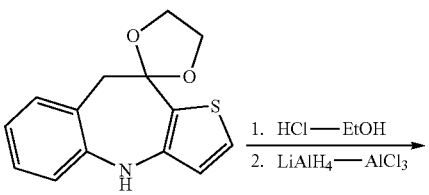
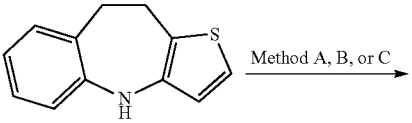
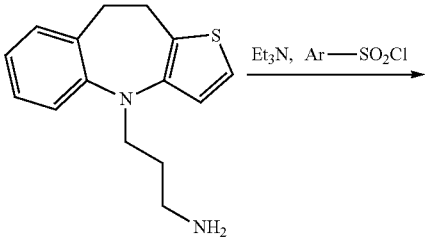
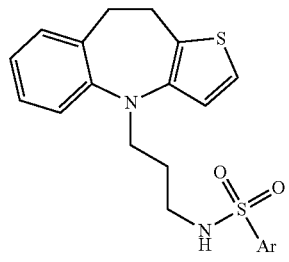

Scheme 7

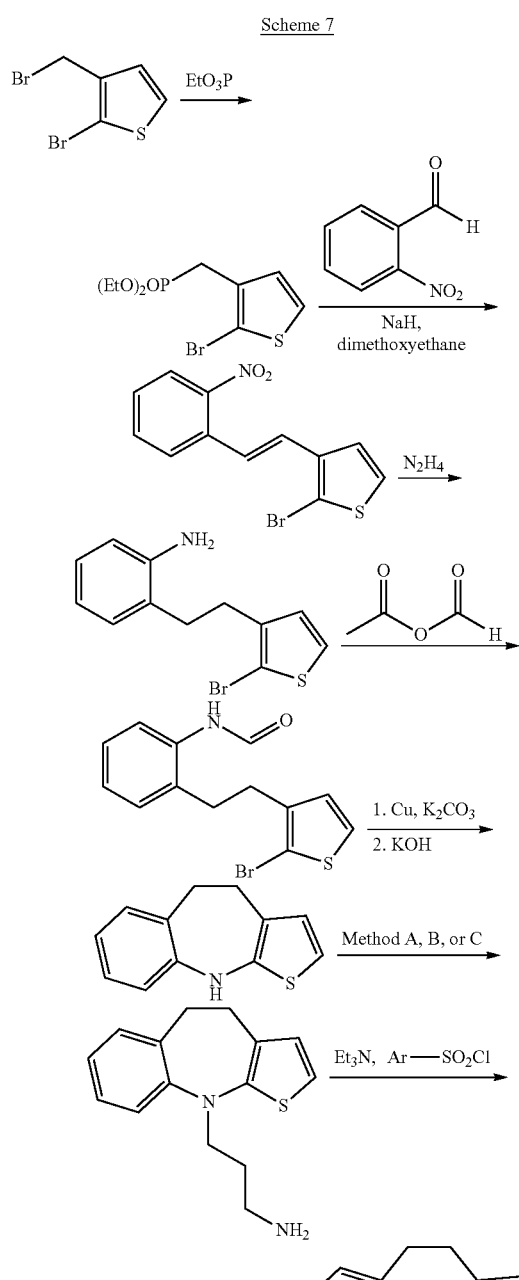

Methods A, B and C referred to in Schemes 3-7 above are three separate approaches to alkylating the nitrogen of the azepine ring. Method A is illustrated in Scheme 1 and proceeds by acylation with chloroacetyl chloride, displacement with cyanide and reduction. Method B is illustrated in Scheme 2 and proceeds by addition of acrylonitrile and reduction. Method C is illustrated in PCT US2012/051097, the synthetic schemes and experimental descriptions of which are incorporated herein by reference. In Method C, the nitrogen of the azepine ring is alkylated with N-(4-bromopropyl)phthalimide, and the phthalimide is cleaved with hydrazine.

By replacing the ortho-chloroaminopyridines in Schemes 2, 3, 4 and 5 with the corresponding known or commercially available ortho-chloroaminoheterocycles, other ring systems can replace the pyridine ring. For example, by replacing 3-amino-4-chloropyridine in Scheme 3 with 5-amino-4-chloropyrimidine, one may obtain compounds in the series:

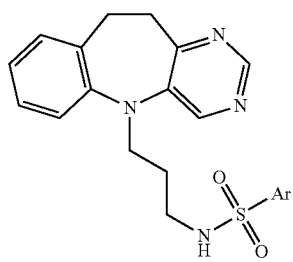

Examples of additional commercially available ortho-chloroaminodiazines that can be used to provide the corresponding diazinobenzazepines include: 2-amino-3-chloropyrazine, 4-amino-3-chloropyridazine, 5-amino-4-chloropyridazine and 4-amino-5-chloropyrimidine.

Syntheses of compounds in which the side chain is hydroxylated may be accomplished according to Scheme 8:

Scheme 8

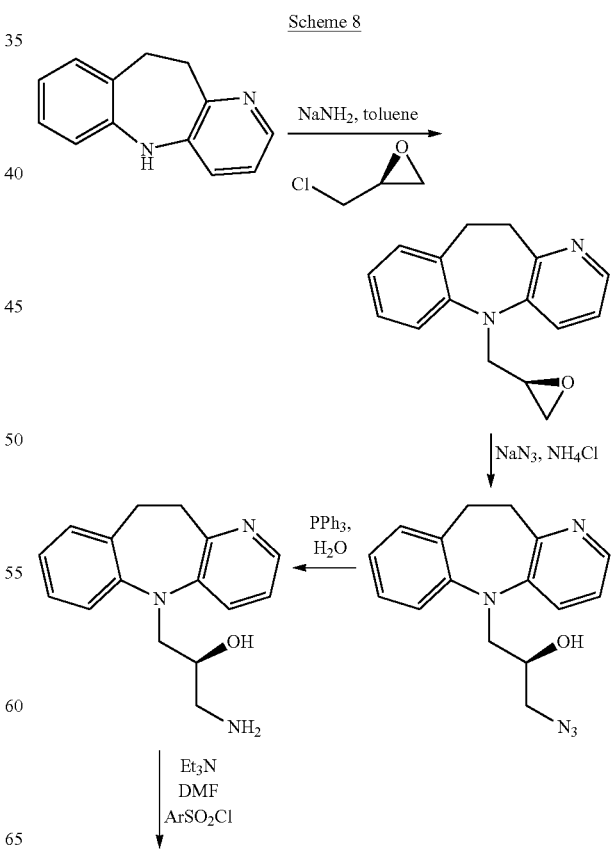

-continued

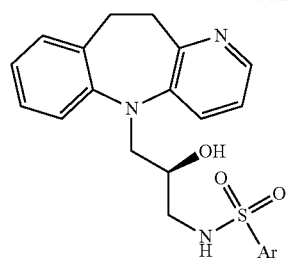

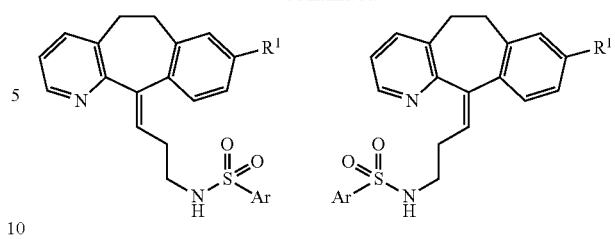

Syntheses of ring systems of formula I wherein Y is other than nitrogen, may be accomplished by methods known in the art, particularly by analogy to the synthetic schemes and experimental descriptions set forth in PCT US2012/051097, WO2006/116157 and WO2003/022835, the synthetic schemes and experimental descriptions of which are incorporated herein by reference.

By the methods of Scheme 9 and 10, compounds may be synthesized in which Y is

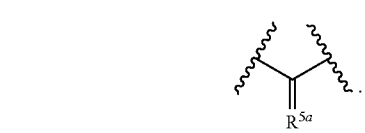

Scheme 9

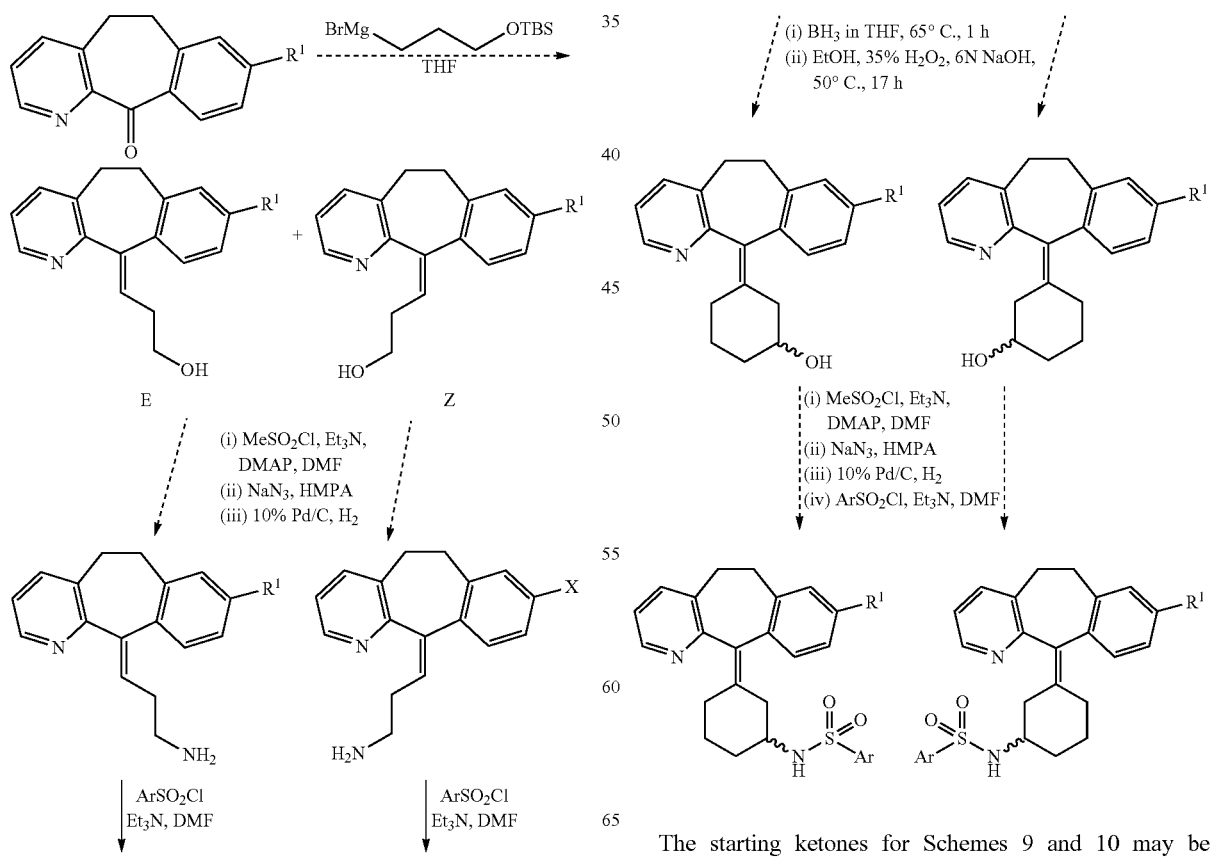

Scheme 10

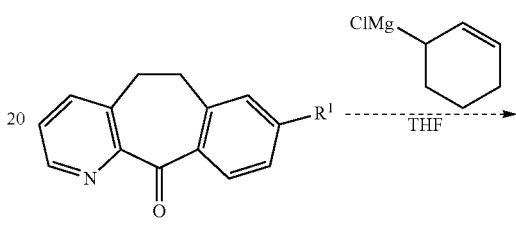

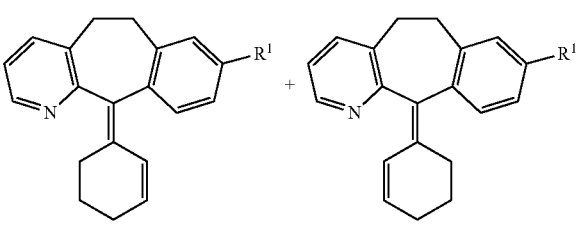

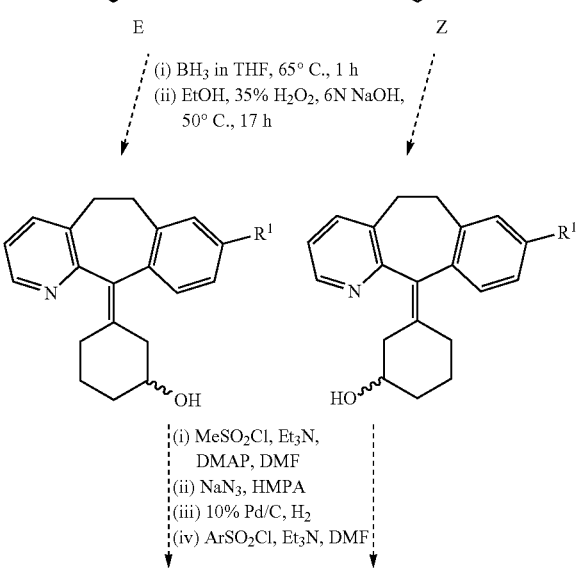

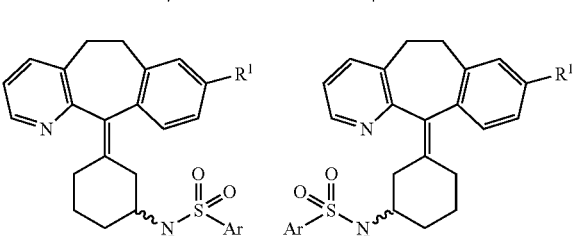

The starting ketones for Schemes 9 and 10 may be obtained from known ortho-methyl nitriles via Scheme 11:

Scheme 11

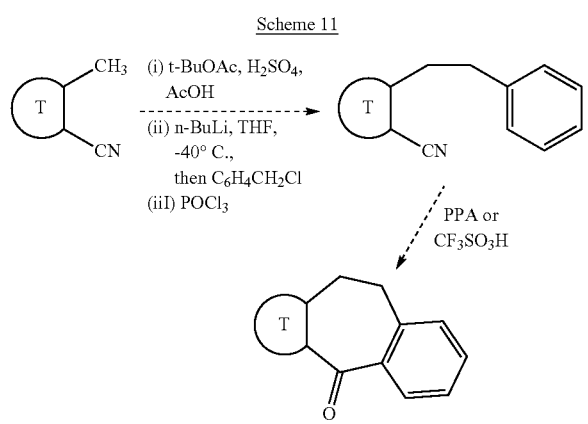

Ortho-amino nitriles known in the art and suitable for use in Scheme 11 include:

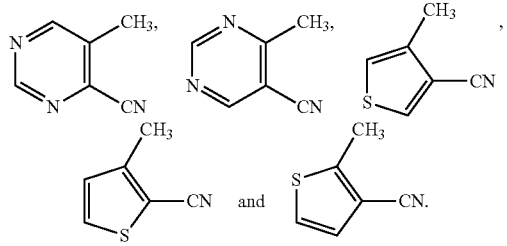

EXAMPLES

Example 100

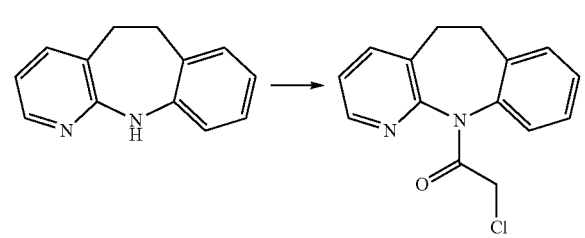 [SMILES: c1ccc2c(c1)CCc1cccnc1N2 ; O=C(CCl)N1c2ccccc2CCc2cccnc21]

1-(5H-Benzo[b]pyrido[3,2-f]azepin-11(6H)-yl)-2-chloroethanone

A solution of 6,11-dihydro-5H-benzo[b]pyrido[3,2-f]azepine (0.150 g, 0.764 mmol) in 1:1 toluene-$CH_2C_{12}$, prepared according to a literature method (Villani, F. J.; Mann, T. A. J. Med. Chem. 1968, 11(4), 894-5) was treated with chloroacetyl chloride (85.1 μL, 1.07 mmol) and heated to 100° C. for 1 h. The mixture was cooled to 25° C., concentrated in vacuo to remove most of the solvent. The residue is suspended in a minimal amount of $CH_2C_{12}$ and purified by flash chromatography ($SiO_2$, 0-25% hexanes-ethyl acetate) to afford the title compound as a beige oil (0.053 g, 25%). $^1$H NMR (600 MHz, $CDCl_3$) δ (mixture of rotamers) 9.15 (0.5H, d, J=4.8 Hz), 8.24 (1H, d, J=4.8 Hz), 8.01 (0.5H, d, J=7.2 Hz), 7.63 (0.5H, br s). 7.48 (1H, dd, J=7.8, 1.2 Hz), 7.44 (0.5H, t, J=6.6 Hz), 7.35-7.37 (1H, m), 7.17-7.20 (2H, m), 7.15 (1H, dd, J=7.2, 4.2 Hz), 6.05 (1H, br s), 4.23, (2H, br s), 3.05 (4H, br s); LCMS m/z 273.1306 ([M+H$^+$], $C_{15}H_{13}ClN_2O$ requires 273.0789).

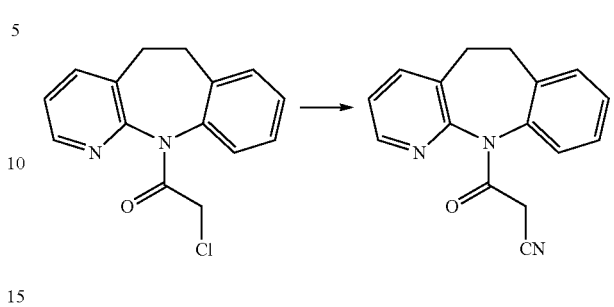

3-(5H-Benzo[b]pyrido[3,2-f]azepin-11(6H)-yl)-3-oxopropanenitrile

A solution of 1-(5H-benzo[b]pyrido[3,2-f]azepin-11(6H)-yl)-2-chloroethanone (1.45 g, 5.32 mmol) in DMF (5.0 mL) was cooled to 0° C. and treated with finely ground sodium cyanide (0.518 g, 10.6 mmol). The mixture was stirred for 14 h at 25° C. The solution was diluted with $CH_2C_{12}$ (500 mL) and washed with $H_2O$ (3×200 mL), saturated aqueous NaCl (200 mL), dried ($Na_2SO_4$), and concentrated in vacuo. The residue was suspended in a minimal amount of $CH_2C_{12}$ and purified by flash chromatography ($SiO_2$, 0-40% hexanes-ethyl acetate) to afford the title compound as a beige solid (0.560 g, 40%). $^1$H NMR (600 MHz, $CDCl_3$) δ (as a mixture of rotamers) 8.34 (1H, d, J=3.6 Hz), 7.57 (1H, d, J=7.8 Hz), 7.42-7.43 (1H, m), 7.26-7.30 (3H, m), 7.25 (1H, dd, J=8.4, 5.4 Hz), 3.78 (2H, br s), 3.41 (2H, br s), 2.95 (2H, br s); $^{13}$C NMR (150 MHz, $CDCl_3$) δ 162.1, 151.0, 147.0, 141.1, 139.7, 136.3, 131.1, 129.7, 129.0, 128.3, 127.6, 124.3, 113.9, 31.4, 29.4, 26.7; LCMS m/z 264.2823 ([M+H$^+$], $C_{16}H_{13}N_3O$ requires 264.1131).

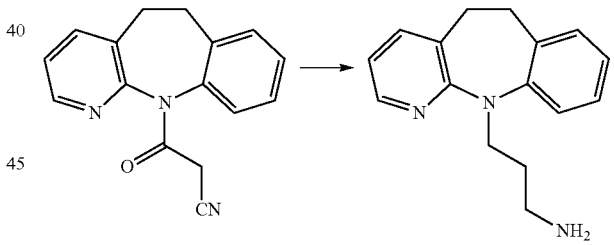

3-(5H-Benzo[b]pyrido[3,2-f]azepin-11(6H)-yl)propan-1-amine

A solution of 3-(5H-benzo[b]pyrido[3,2-f]azepin-11(6H)-yl)-3-oxopropanenitrile (0.560 g, 2.13 mmol) in THF (10.0 mL) was cooled to 0° C. and treated with a $BH_3$-THF (1 M solution in THF, 8.50 mL, 8.50 mmol). The flask was sealed, heated to 70° C. for 5 h, and then cooled to 0° C. The solution was treated slowly, dropwise with a solution of aqueous 1 M HCl (8.5 mL), stirred for an additional 0.5 h at to 0° C., and then heated to 70° C. for 1 h. The mixture was cooled to 25° C., treated with aqueous 4 M NaOH until pH>8, and extracted with THF (3×100 mL). The combined extracts were concentrated to dryness. The residue was dissolved in a minimal amount of $CH_2C_{12}$ and purified by flash chromatography ($SiO_2$, 0-50% hexanes-ethyl acetate to remove nonpolar impurities followed by 17:2:1 $CH_2C_{12}$:

MeOH:NH₄OH to elute the product). The combined fractions of pure product were concentrated, dried azeotropically with toluene to afford the title compound as a clear oil (0.267 g, 49%). ¹H NMR (600 MHz, CDCl₃) δ 8.09 (1H, dd, J=4.8, 1.8 Hz), 7.25 (1H, dd, J=7.2, 1.2 Hz), 7.17-7.18 (2H, m), 7.14 (1H, d, J=7.8 Hz), 7.02-7.04 (1H, m), 6.70 (1H, dd, J=7.8, 4.8 Hz), 4.09 (2H, t, J=6.6 Hz), 3.09-3.11 (2H, m), 3.06-3.07 (2H, m), 2.98 (2H, m), 2.75 (2H, (2H, t, J=6.6 Hz), 1.78 (2H, quintet, J=6.6 Hz). ¹³C NMR (150 MHz, CDCl₃) δ 156.3, 147.4, 144.8, 139.5, 138.3, 128.3, 126.9, 124.4, 124.0, 122.9, 116.2, 47.6, 39.8, 34.7, 31.7, 30.8; LCMS m/z 254.2144 ([M+H⁺], $C_{16}H_{19}N_3$ requires 254.1652).

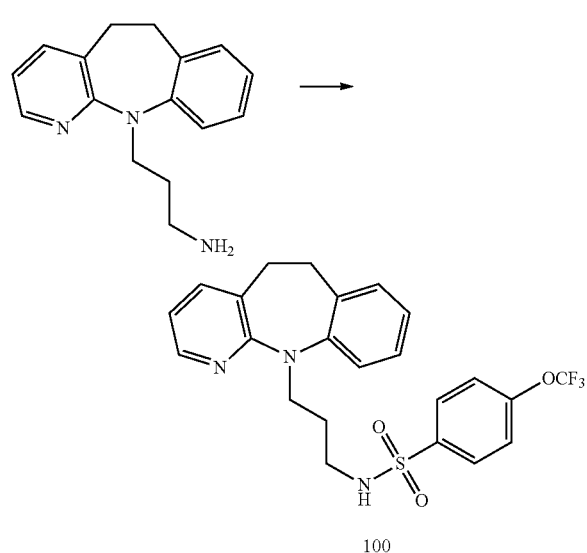

100

N-(3-(5H-Benzo[b]pyrido[3,2-f]azepin-11(6H)-yl)propyl)-4-(trifluoromethoxy)benzenesulfonamide A solution of 3-(5H-benzo[b]pyrido[3,2-f]azepin-11(6H)-yl)propan-1-amine (0.080 g, 0.316 mmol) in DMF (1.0 mL) was cooled to 0° C., treated with Et₃N (48.0 μL, 0.348 mmol), and 4-trifluoromethoxybenzenesulfonyl chloride (56.0 μL, 0.332 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (3×50 mL), dried (Na₂SO₄), and concentrated in vacuo. The residue was dissolved in a minimal amount of CH₂Cl₂ and purified by flash chromatography (SiO₂, 0-30% hexanes-ethyl acetate). The purified fractions were combined, dissolved in a minimal amount of ethyl acetate and were precipitated with the addition of hexanes to afford the title compound as a white solid (0.078 g, 52%). ¹H NMR (600 MHz, CDCl₃) δ 8.02 (1H, dd, J=4.8, 1.8 Hz), 7.74 (2H, d, J=7.2 Hz), 7.16-7.18 (3H, m), 7.07 (1H, td, J=7.2 Hz), 7.03 (1H, d, J=7.2 Hz), 6.94-6.97 (2H, m), 6.64 (1H, dd, J=7.2, 4.8 Hz), 6.22 (1H, br s), 3.86 (2H, t, J=6.6 Hz), 2.93-2.95 (2H, m), 2.91-2.93 (2H, m), 2.89-2.91 (2H, m), 1.74 (2H, quintet, J=6.6 Hz); ¹³C NMR (150 MHz, CDCl₃) δ 155.6, 152.0, 147.3, 144.5, 140.0, 138.6, 138.2, 129.3, 127.1, 124.8, 124.0, 122.8, 121.0, 119.6, 116.2, 47.8, 41.5, 35.1, 30.9, 28.3; LCMS m/z 478.7886 ([M+H⁺], $C_{23}H_{22}ClF_3N_3O_3S$ requires 478.1407).

Example 101

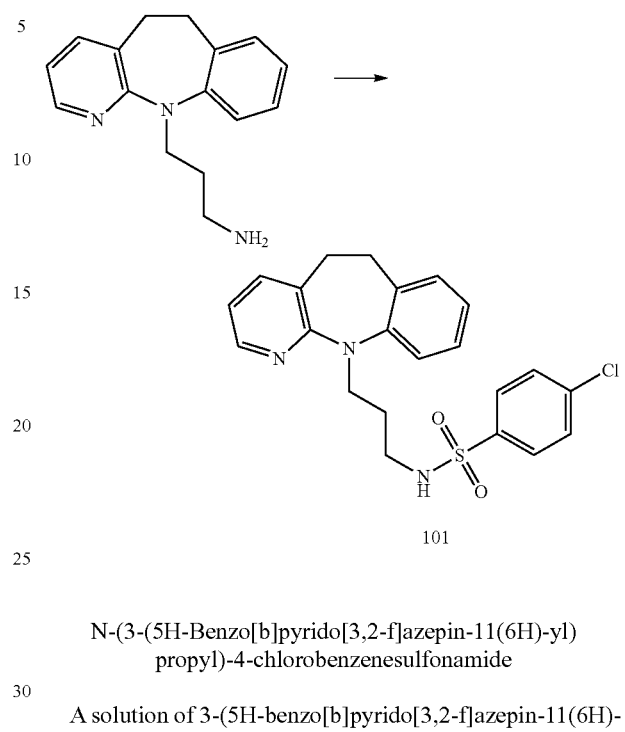

N-(3-(5H-Benzo[b]pyrido[3,2-f]azepin-11(6H)-yl)propyl)-4-chlorobenzenesulfonamide A solution of 3-(5H-benzo[b]pyrido[3,2-f]azepin-11(6H)-yl)propan-1-amine (0.0800 g, 0.316 mmol) in DMF (1.0 mL) was cooled to 0° C., treated with Et₃N (48.0 μL, 0.348 mmol), and 4-chlorobenzenesulfonyl chloride (0.0700 g, 0.348 mmol). The mixture was warmed to 25° C. and stirred for 2 h. The mixture was partitioned between saturated aqueous NaCl (50 mL), and CH₂Cl₂ (100 mL). The organic layer was washed with saturated aqueous NaCl (3×50 mL), dried (Na₂SO₄), and concentrated in vacuo. The residue was dissolved in a minimal amount of CH₂Cl₂ and purified by flash chromatography (SiO₂, 0-30% hexanes-ethyl acetate). The purified fractions were combined, dissolved in a minimal amount of ethyl acetate and were precipitated with the addition of hexanes to afford the title compound as a white solid (0.067 g, 49%). ¹H NMR (600 MHz, CDCl₃) δ 7.61 (2H, dd, J=9.0, 1.8 Hz), 7.28 (2H, dd, J=8.5, 1.6 Hz), 7.17 (1H, d, J=7.2 Hz), 7.07 (1H, tt, J=8.4, 1.8 Hz), 7.03 (1H, td, J=7.2, 1.8 Hz), 6.96 (1H, t, J=1.2 Hz), 6.94 (1H, d, J=1.8 Hz), 6.63-6.65 (1H, m), 6.11 (1H, br s), 3.84 (2H, t, J=6.0 Hz), 2.93-2.94 (2H, m), 2.90-2.93 (2H, m), 2.87-2.90 (2H, m), 1.71 (2H, quintet, J=6.6 Hz); ¹³C NMR (150 MHz, CDCl₃) δ 155.6, 147.2, 144.5, 139.9, 138.9, 138.7, 138.2, 129.4, 128.7, 128.3, 127.1, 124.7, 124.0, 122.8, 116.2, 47.7, 41.4, 35.1, 30.9, 28.3; LCMS m/z 428.4579 ([M+H⁺], $C_{22}H_{22}ClN_3O_2S$ requires 428.1194).

Example 102

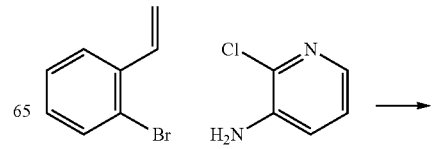

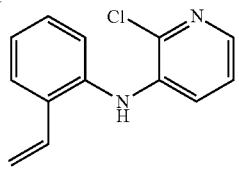

2-Chloro-N-(2-vinylphenyl)pyridin-3-amine

A solution of 2-chloropyridin-3-amine (5.43 g, 42.2 mmol) in dioxane (80.0 mL) was treated with 2-bromostyrene (5.20 mL, 40.2 mmol), $Pd_2(dba)_3$ (0.277 g, 0.302 mmol), and Davephos (0.356 g, 0.905 mmol). The solution was degassed for several minutes with Ar(g) and heated to 110° C. for 14 h. The solution was cooled to 25° C., concentrated in vacuo, then partitioned between saturated aqueous NaCl (500 mL), and $CH_2Cl_2$ (1000 mL). The organic phase was washed with saturated aqueous NaCl (2×300 mL), dried ($Na_2SO_4$), and concentrated in vacuo. The residue was dissolved in a minimal amount of $CH_2Cl_2$ and purified by flash chromatography ($SiO_2$, 0-10% hexanes-ethyl acetate) to afford the title compound which crystallized slowly upon standing to provide a beige solid (3.59 g, 39%). $^1$H NMR (600 MHz, $CDCl_3$) δ 7.84 (1H, q, J=1.8 Hz), 7.61 (1H, d, J=7.8 Hz), 7.31 (1H, t, J=7.8 Hz), 7.21-7.25 (2H, m), 7.02-7.06 (2H, m), 6.83 (1H, dd, J=17.4, 11.4 Hz), 6.02 (1H, s), 5.76 (1H, d, J=18.0 Hz), 5.34 (1H, d, J=11.4 Hz); $^{13}$C NMR (150 MHz, $CDCl_3$) δ 139.95, 138.89, 138.1, 137.1, 133.4, 132.4, 129.1, 127.3, 125.9, 124.5, 123.3, 121.1, 117.1; LCMS m/z 231.1964 ([M+H$^+$], $C_{13}H_{11}ClN_2$ requires 231.0684).

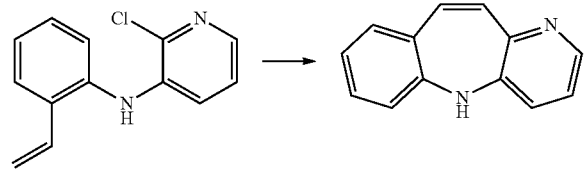 [SMILES: C=Cc1ccccc1Nc1cccnc1Cl ; C1=Cc2ncccc2Nc2ccccc21]

5H-Benzo[b]pyrido[2,3-f]azepine

A solution of 2-chloro-N-(2-vinylphenyl)pyridin-3-amine (1.46 g, 6.33 mmol) in 1:1 DMF-$Et_3$N (6.0 mL) was treated with $Pd(OAc)_2$ (0.142 g, 0.633 mmol) and tri-o-tolylphosphine (0.578 g, 1.90 mmol). The solution was heated in a microwave to 150° C. for 2 h and then cooled to 25° C. The mixture was partitioned between saturated aqueous NaCl (100 mL), and $CH_2Cl_2$ (300 mL). The organic layer was washed with saturated aqueous NaCl (3×200 mL), dried ($Na_2SO_4$), and concentrated in vacuo. The residue was dissolved in a minimal amount of $CH_2Cl_2$ and purified by flash chromatography ($SiO_2$, 0-30% hexanes-ethyl acetate). The purified fractions were combined, dissolved in a minimal amount of ethyl acetate and precipitated with the addition of hexanes to afford the title compound as a yellow solid (0.579 g, 47%). $^1$H NMR (600 MHz, $CDCl_3$) δ 8.06 (1H, d, J=4.8 Hz), 7.05 (2H, td, J=9.0, 1.2 Hz), 6.49 (1H, d, J=7.8 Hz), 6.47 (1H, d, J=3.6 Hz), 4.84 (1H, br s); $^{13}$C NMR (150 MHz, $CDCl_3$) δ 149.7, 148.1, 144.8, 143.9, 135.2, 133.5, 131.4, 130.2, 129.4, 126.0, 123.8, 123.7, 119.5; LCMS m/z 195.1824 ([M+H$^+$], $C_{13}H_{10}N_2$ requires 195.0917).

10,11-Dihydro-5H-benzo[b]pyrido[2,3-f]azepine

A solution of 5H-benzo[b]pyrido[2,3-f]azepine (1.60 g, 8.23 mmol) in 1:1 THF-MeOH (10.0 mL) was treated with 10% Pd/C (0.712 g, 0.823 mmol), placed under an atmosphere of $H_2$ (g), and stirred for 6 h at 25° C. The mixture was filtered thru Celite and concentrated in vacuo. The residue was dissolved in a minimal amount of $Et_2O$ and precipitated with the addition of hexanes to afford the title compound as a beige solid (1.55 g, 96%). $^1$H NMR (600 MHz, $CDCl_3$) δ 8.03 (1H, d, J=1.8 Hz), 7.10-7.12 (2H, m), 7.03-7.05 (2H, m), 6.85 (1H, d, J=7.2 Hz), 6.79 (1H, d, J=7.8 Hz), 6.00 (1H, s), 3.32 (2H, t, J=5.4 Hz), 3.13 (2H, t, J=5.4 Hz); $^{13}$C NMR (150 MHz, $CDCl_3$) δ 147.7, 142.1, 139.9, 139.0, 130.7, 129.8, 127.2, 124.8, 122.0, 120.8, 118.4, 38.5, 33.2; LCMS m/z 197.1975 ([M+H$^+$], $C_{13}H_{12}N_2$ requires 197.1073).

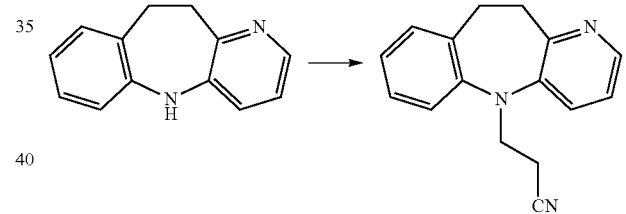

3-(10,11-Dihydro-5H-benzo[b]pyrido[2,3-f]azepin-5-yl)propanenitrile

A solution of 10,11-dihydro-5H-benzo[b]pyrido[2,3-f]azepine (1.00 g, 5.09 mmol) in toluene (5.0 mL) was treated with acrylonitrile (5.0 mL), Triton B (0.5 mL), and warmed to 80° C. for 2 h. The mixture was cooled to 25° C., concentrated under a stream of $N_2$ (g), resuspended in a minimal amount of toluene and purified by flash chromatography ($SiO_2$, 0-25% hexanes-ethyl acetate). The purified fractions were combined, dissolved in a minimal amount of ethyl acetate, and precipitated with the addition of hexanes to afford the title compound as a white solid (0.400 g, 32%). $^1$H NMR (600 MHz, $CDCl_3$) δ 7.35-7.36 (1H, m), 7.29 (1H, dd, J=8.4, 1.2 Hz), 7.25 (1H, d, J=7.2 Hz), 7.20 (1H, td, J=7.2, 1.2 Hz), 7.08-7.10 (2H, m), 7.05 (1H, d, J=8.4 Hz), 4.06 (2H, t, J=6.6 Hz), 3.33-3.36 (2H, m), 3.29-3.31 (2H, m), 2.62 (2H, t, J=6.6 Hz); $^{13}$C NMR (150 MHz, $CDCl_3$) δ 153.4, 146.5, 143.2, 137.9, 129.9, 128.7, 127.2, 125.9, 125.2, 121.6, 120.6, 118.2, 46.6, 36.5, 30.0, 17.3; LCMS m/z 250.1808 ([M+H$^+$], $C_{16}H_{15}N_3$ requires 250.1339).

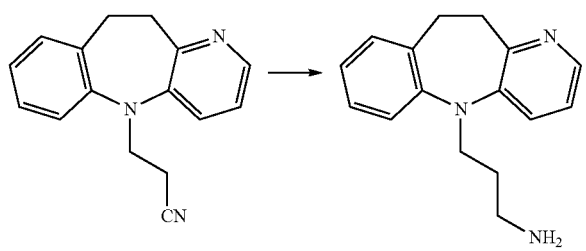 [SMILES: N#CCCN1c2ccccc2CCc2ncccc21 ; NCCCN1c2ccccc2CCc2ncccc21]

3-(10,11-Dihydro-5H-benzo[b]pyrido[2,3-f]azepin-5-yl)propan-1-amine

A solution of 3-(10,11-dihydro-5H-benzo[b]pyrido[2,3-f]azepin-5-yl)propanenitrile (0.400 g, 1.60 mmol) in THF (10.0 mL) was cooled to 0° C. and treated with BH$_3$-THF (1 M solution in THF, 6.40 mL, 6.40 mmol). The flask was sealed, heated to 70° C. for 5 h, and then cooled to 0° C. The solution was treated slowly, dropwise with a solution of aqueous 1 M HCl (6.40 mL), stirred for an additional 0.5 h at 0° C., and then heated to 70° C. for 1 h. The mixture was cooled to 25° C., treated with aqueous 4 M NaOH until pH>8, and then extracted with THF (3×100 mL). The combined extracts were concentrated to dryness. The residue was dissolved in a minimal amount of CH$_2$C$_{12}$ and purified by flash chromatography (SiO$_2$, 0-50% hexanes-ethyl acetate to remove nonpolar impurities followed by 17:2:1 CH$_2$C$_{12}$:MeOH:NH$_4$OH to elute the product). The combined fractions of pure product were concentrated, dried azeotropically with toluene to afford the title compound as a clear oil (0.181 g, 45%). $^1$H NMR (600 MHz, CDCl$_3$) δ 8.07 (1H, dd, J=4.2, 1.2 Hz), 7.32 (1H, dd, J=8.4, 1.2 Hz), 7.14-7.18 (2H, m), 7.06 (1H, d, J=7.8 Hz), 7.02 (1H, dd, J=8.4, 4.2 Hz), 7.00 (1H, td, J=7.8, 0.6 Hz), 3.77 (2H, t, J=6.6 Hz), 3.29 (2H, t, J=6.6 Hz), 3.19 (2H, t, J=6.6 Hz), 2.71 (2H, t, J=6.6 Hz), 2.17 (2H, br s), 1.70 (2H, t, J=6.6 Hz); $^{13}$C NMR (150 MHz, CDCl$_3$) δ 152.6, 148.2, 144.2, 141.9, 136.8, 129.2, 126.8, 126.1, 124.0, 121.4, 120.9, 47.8, 39.8, 36.6, 31.3, 30.2; LCMS m/z 254.2198 ([M+H$^+$], C$_{16}$H$_{19}$N$_3$ requires 254.1652).

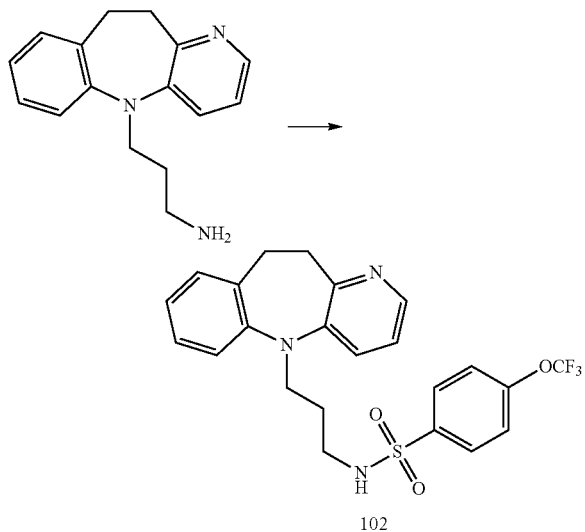

102

N-(3-(10,11-Dihydro-5H-benzo[b]pyrido[2,3-f]azepin-5-yl)propyl)-4-(trifluoromethoxy)benzenesulfonamide A solution of 3-(10,11-dihydro-5H-benzo[b]pyrido[2,3-f]azepin-5-yl)propan-1-amine (0.060 g, 0.237 mmol) in DMF (1.0 mL) was cooled to 0° C., treated with Et$_3$N (36.0 μL, 0.261 mmol), and 4-trifluoromethoxybenzenesulfonyl chloride (42.0 μL, 0.249 mmol). The mixture was warmed to 25° C. and stirred for 2 h. The mixture was partitioned between saturated aqueous NaCl (50 mL), and CH$_2$C$_{12}$ (100 mL). The organic layer was washed with saturated aqueous NaCl (3×50 mL), dried (Na$_2$SO$_4$), and concentrated in vacuo. The residue was dissolved in a minimal amount of CH$_2$C$_{12}$ and purified by flash chromatography (SiO$_2$, 0-30% hexanes-ethyl acetate). The purified fractions were combined, dissolved in a minimal amount of ethyl acetate and were precipitated with the addition of hexanes to afford the title compound as a white solid (0.065 g, 57%). $^1$H NMR (600 MHz, CDCl$_3$) δ 8.04 (1H, dd, J=4.6, 1.0 Hz), 7.80 (2H, d, J=7.2 Hz), 7.28 (1H, d, J=7.8 Hz), 7.26 (2H, d, J=9.0 Hz), 7.15-7.18 (2H, m), 7.02-7.04 (3H, m), 5.40 (1H, s), 3.75 (2H, t, J=6.6 Hz), 3.19 (2H, t, J=6.0 Hz), 3.04 (2H, t, J=6.0 Hz), 3.00 (2H, t, J=6.6 Hz), 1.78 (2H, t, J=6.6 Hz); $^{13}$C NMR (150 MHz, CDCl$_3$) δ 152.5, 152.2, 147.5, 144.2, 142.2, 138.5, 136.8, 129.5, 129.3, 127.1, 126.1, 124.5, 121.6, 121.4, 121.1, 120.8, 46.9, 41.0, 36.4, 30.1, 27.7; LCMS m/z 478.3604 ([M+H$^+$], C$_{23}$H$_{22}$ClF$_3$N$_3$O$_3$S requires 478.1407).

Example 103

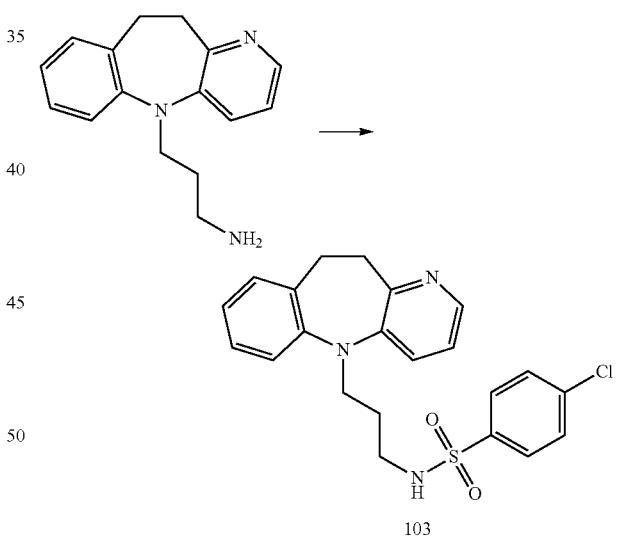

103

4-Chloro-N-(3-(10,11-dihydro-5H-benzo[b]pyrido[2,3-f]azepin-5-yl)propyl)benzenesulfonamide A solution of 3-(10,11-dihydro-5H-benzo[b]pyrido[2,3-f]azepin-5-yl)propan-1-amine (0.0600 g, 0.237 mmol) in DMF (1.0 mL) was cooled to 0° C., treated with Et$_3$N (36.0 μL, 0.261 mmol), and 4-chlorobenzenesulfonyl chloride (0.0530 g, 0.249 mmol). The mixture was warmed to 25° C. and stirred for 2 h. The mixture was partitioned between saturated aqueous NaCl (50 mL), and CH$_2$C$_{12}$ (100 mL). The organic layer was washed with saturated aqueous NaCl (3×50 mL), dried (Na₂SO₄), and concentrated in vacuo. The residue was dissolved in a minimal amount of CH$_2$C$_{12}$ and purified by flash chromatography (SiO$_2$, 0-30% hexanes-ethyl acetate). The purified fractions were combined, dissolved in a minimal amount of ethyl acetate and were precipitated with the addition of hexanes to afford the title compound as a white solid (0.059 g, 58%). $^1$H NMR (600 MHz, CDCl$_3$) δ 8.06 (1H, dd, J=4.8, 1.2 Hz), 7.68 (2H, d, J=8.4 Hz), 7.40 (2H, d, J=8.4 Hz), 7.26 (1H, d, J=7.8 Hz), 7.15-7.17 (2H, m), 7.02-7.05 (2H, m), 7.02 (1H, s), 5.22 (1H, t, J=5.4 Hz), 3.73 (2H, t, J=6.6 Hz), 3.19 (2H, t, J=6.0 Hz), 3.04 (2H, t, J=6.6 Hz), 2.98 (2H, q, J=6.0 Hz), 1.75 (2H, quintet, J=6.0 Hz); $^{13}$C NMR (150 MHz, CDCl$_3$) δ 152.6, 147.5, 144.2, 142.2, 139.3, 138.6, 136.8, 129.6, 129.5, 128.6, 127.0, 126.0, 124.5, 121.6, 120.8, 46.9, 41.0, 36.5, 30.2, 27.7; LCMS m/z 428.2336 ([M+H⁺], C$_{22}$H$_{22}$ClN$_3$O$_2$S requires 428.1194).

Example 104

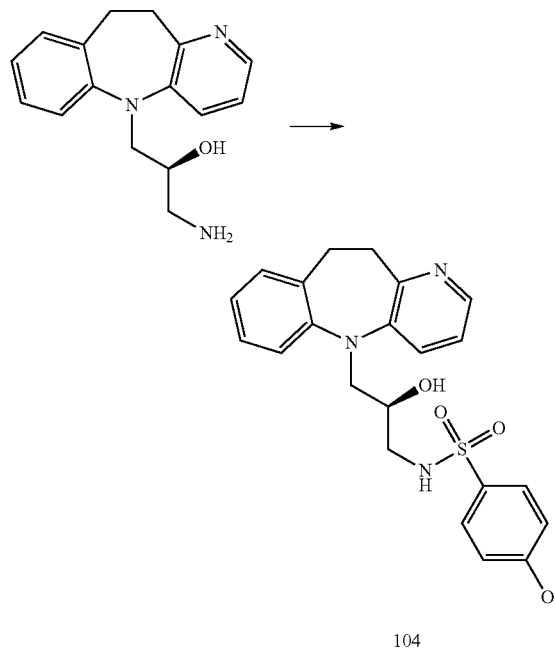

104

(R)—N-(3-(10,11-dihydro-5H-benzo[b]pyrido[2,3-f] azepin-5-yl)-2-hydroxypropyl)-4-(trifluoromethoxy) benzenesulfonamide A solution of (5)-1-amino-3-(10,11-dihydro-5H-benzo[b] pyrido[2,3-f]azepin-5-yl)propan-2-ol (0.056 g, 0.208 mmol) in DMF (1.0 mL) was cooled to 0° C., treated with Et$_3$N (30.0 μL, 0.218 mmol), and 4-trifluoromethoxybenzenesulfonyl chloride (37.0 μL, 0.218 mmol). The mixture was warmed to 25° C. and stirred for 2 h. The mixture was partitioned between saturated aqueous NaCl (50 mL), and CH$_2$C$_{12}$ (100 mL). The organic layer was washed with saturated aqueous NaCl (3×50 mL), dried (Na$_2$SO$_4$), and concentrated in vacuo. The residue was dissolved in a minimal amount of CH$_2$C$_{12}$ and purified by flash chromatography (SiO$_2$, 0-30% hexanes-ethyl acetate). The purified fractions were combined, dissolved in a minimal amount of ethyl acetate and were precipitated with the addition of hexanes to afford the title compound as a clear film (0.061 g, 59%). $^1$H NMR (600 MHz, CDCl$_3$) δ 7.97 (1H, d, J=4.8 Hz), 7.78 (2H, d, J=6.6 Hz), 7.30 (1H, d, J=7.8 Hz), 7.21 (2H, d, J=8.4 Hz), 7.10-7.14 (2H, m), 7.01-7.04 (2H, m), 6.97 (1H, dd, J=7.8, 4.8 Hz), 6.28 (1H, br s), 3.81 (1H, dd, J=6.0, 3.0 Hz), 3.77 (1H, d, J=6.6 Hz), 3.69 (1H, dd, J=12.6, 6.0 Hz), 3.17-3.20 (1H, m), 3.12-3.14 (2H, m), 3.05-3.07 (2H, m), 2.92-2.95 (1H, m); $^{13}$C NMR (150 MHz, CDCl$_3$) δ 152.4, 152.1, 147.7, 144.0, 142.1, 138.4, 136.6, 129.4, 129.2, 127.2, 126.5, 124.8, 121.7, 121.2, 121.1, 120.8, 67.1, 54.0, 47.1, 36.7, 36.2; LCMS m/z 494.6078 ([M+H⁺], C$_{23}$H$_{22}$F$_3$N$_3$O$_4$S requires 494.5061).

Example 105

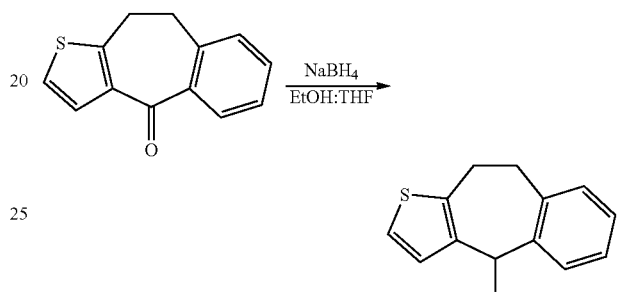

9,10-dihydro-4H-benzo[4,5]cyclohepta[1,2-b]thiophen-4-ol

To a solution of 9,10-dihydro-4H-benzo[4,5]cyclohepta [1,2-b]thiophen-4-one (5.70 g, 26.6 mmol) in ethanol (106 mL), and THF (42 mL), was added sodium borohydride (4.02 g, 106 mmol) slowly. The reaction mixture was brought to boiling, and then stirred at 80° C. for 10 min, and at RT for 18 h, in a sealed vessel. The mixture was poured in to ice water, treated with sat. aq. NH$_4$Cl solution, concentrated to remove EtOH, and THF, extracted with DCM, concentrated to give 9,10-dihydro-4H-benzo[4,5]cyclohepta [1,2-b]thiophen-4-ol (5.69 g, 99%). $^1$H NMR (600 MHz, DMSO-d$^6$) δ 7.39-7.38 (1H, m), 7.24-7.23 (1H, m), 7.20-7.17 (2H, m), 7.06 (1H, d, J=5.4 Hz), 5.89-5.87 (2H, m), 3.34-3.30 (1H, m), 3.12-3.02 (2H, m), 2.97-2.92 (1H, m); $^{13}$C NMR (150 MHz, DMSO-d$^6$) δ 145.1, 140.3, 139.2, 136.7, 129.5, 129.1, 127.6, 126.5, 125.3, 121.9, 69.4, 31.1, 29.1.

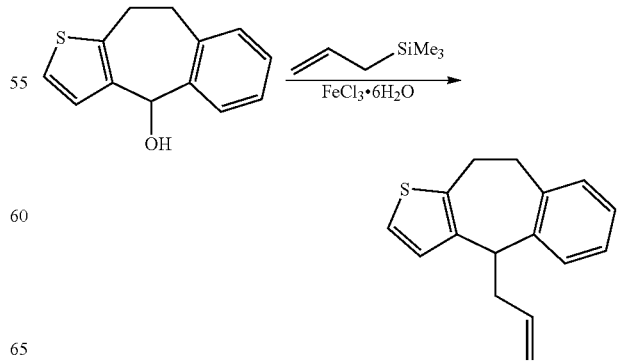

4-allyl-9,10-dihydro-4H-benzo[4,5]cyclohepta[1,2-b]thiophene

To a solution of 9,10-dihydro-4H-benzo[4,5]cyclohepta[1,2-b]thiophen-4-ol (0.101 g, 0.481 mmol) in dry DCM (1 mL) at 0° C., allyltrimethylsilane (0.109 g, 0.962 mmol) and iron(III) chloride hexahydrate (0.007 g, 0.0.024 mmol) were added. The mixture stirred at RT, under argon for 30 min. The solvent was removed under reduced pressure, and the residue was purified by flash chromatography (SiO$_2$, 0% ethylacetate in hexanes) to afford 4-allyl-9,10-dihydro-4H-benzo[4,5]cyclohepta[1,2-b]thiophene (0.050 g, 43%) as a yellow oil.

$^1$H NMR (600 MHz, CDCl$_3$) δ 7.23-7.13 (4H, m), 7.06-7.04 (1H, m), 6.85-6.84 (1H, m), 5.79-5.73 (1H, m), 5.03-4.98 (2H, m), 4.11 (1H, t, J=7.8 Hz), 3.52-3.48 (1H, m), 3.29-3.25 (1H, m), 3.03-2.98 (2H, m), 2.81-2.77 (2H, m); $^{13}$C NMR (150 MHz, CDCl$_3$) δ 142.3, 140.2, 137.7, 130.6, 130.1, 129.7, 127.0, 126.4, 121.2, 116.3, 48.8, 42.5, 33.4, 29.1.

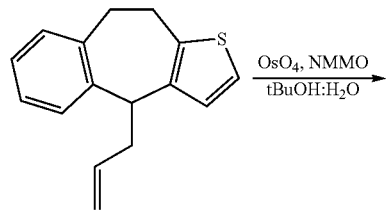

3-(9,10-dihydro-4H-benzo[4,5]cyclohepta[1,2-b]thiophen-4-yl)propane-1,2-diol A solution of 4-allyl-9,10-dihydro-4H-benzo[4,5]cyclohepta[1,2-b]thiophene (0.025 g, 0.104 mmol), osmium tetroxide (0.012 mL, 0.001 mmol, 2.5% in tert-butanol), and N-methylmorpholine N-oxide (0.013 g, 0.114 mmol) in tert-butanol:water (0.5 mL:1 mL) was stirred at RT for 14 h. The reaction mixture was treated with solid sodium bisulfite for 1 h, concentrated, and purified by flash chromatography (SiO$_2$, 2%-10% methanol-dichloromethane) to afford 3-(9,10-dihydro-4H-benzo[4,5]cyclohepta[1,2-b]thiophen-4-yl)propane-1,2-diol (0.027 g, 96%). The diastereomeric ratio was determined to be 1:1.2 by $^1$H NMR analysis. $^1$H NMR (600 MHz, CDCl$_3$) δ 7.24-7.15 (4H, m), 7.05-7.03 (1H, m), 1H [6.90 (d, J=5.4 Hz), 6.86 (d, J=4.8 Hz)], 1H [4.38 (dd, J=10.2, 4.2 Hz), 4.32-4.31 (m)], 1H [3.78-3.76 (m), 3.63 (dd, J=10.3, 3.0 Hz)], 3.52-3.37 (3H, m), 3.26-3.24 (1H, m), 2.96-2.92 (2H, m), 2.18-1.98 (4H, m); $^{13}$C NMR (150 MHz, CDCl$_3$) δ 143.0, 141.3, 140.4, 140.3, 138.1, 137.5, 137.4, 137.0, 131.0, 130.4, 129.2, 127.3, 127.0, 126.6, 121.8, 121.4, 70.7, 70.1, 67.3, 67.1, 44.8, 44.4, 41.4, 33.6, 33.3, 29.0; LCMS m/z 275.1161 ([M+H$^+$], C$_{16}$H$_{19}$O$_2$S requires 275.3853).

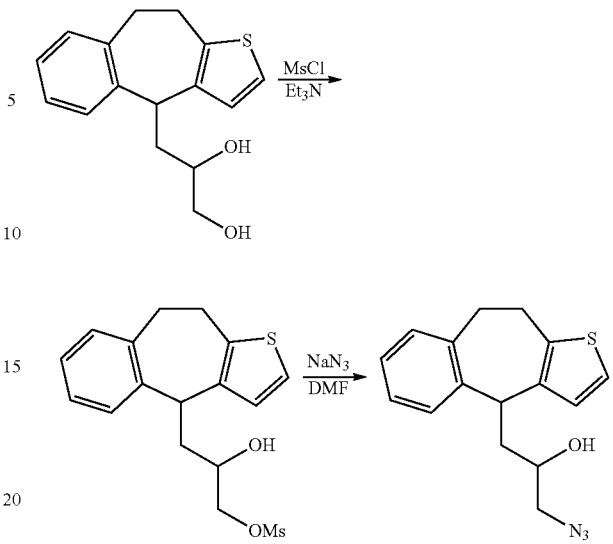

1-azido-3-(9,10-dihydro-4H-benzo[4,5]cyclohepta[1,2-b]thiophen-4-yl)propan-2-ol To a solution 3-(9,10-dihydro-4H-benzo[4,5]cyclohepta[1,2-b]thiophen-4-yl)propane-1,2-diol (2.50 g, 9.11 mmol), and triethylamine (2.50 mL, 18.2 mmol) in DCM (9.0 mL) under argon, at 0° C., was added methane sulfonyl chloride (1.48 mL, 0.843 mmol). The mixture was stirred for 21 h at RT. The reaction mixture was treated with 1 N HCl, extracted with DCM, organic layer was washed with brine, concentrated, to obtain a residue which was purified by flash chromatography (SiO$_2$, 25%-50% ethylacetate-hexanes) to afford crude 3-(9,10-dihydro-4H-benzo[4,5]cyclohepta[1,2-b]thiophen-4-yl)-2-hydroxypropyl methanesulfonate (0.429 g) which was taken to the next step without further purification.

A solution of 3-(9,10-dihydro-4H-benzo[4,5]cyclohepta[1,2-b]thiophen-4-yl)-2-hydroxypropyl methanesulfonate (0.429 g, ~1.22 mmol)), and sodium azide (0.095 g, 1.46 mmol) in DMF (0.3 mL) was heated to 70° C. in a sealed vessel for 1 h. The mixture was cooled to 25° C., brine was added, extracted with DCM, concentrated in vacuo, purified by flash chromatography (SiO$_2$, 10%-20% ethylacetate-hexanes) to afford 1-azido-3-(9,10-dihydro-4H-benzo[4,5]cyclohepta[1,2-b]thiophen-4-yl)propan-2-ol (0.204 g, 8% over two steps). The diastereomeric ratio was determined to be 1:1.2 by $^1$H NMR analysis. $^1$H NMR (600 MHz, CDCl$_3$) δ 7.25-7.18 (4H, m), 7.08-7.06 (1H, m), 1H [6.91 (d, J=5.4 Hz), 6.89 (d, J=4.8 Hz)], 1H [4.41 (dd, J=11.4, 4.8 Hz), 4.33 (d, J=9.6, 6.6 Hz)], 1H [3.85-3.81 (m), 3.56-3.53 (m)], 3.51-3.35 (2H, m), 3.32-3.18 (2H, m), 2.98-2.93 (2H, m), 2.38-2.13 (2H, m), 2.10-2.04 (1H, m); $^{13}$C NMR (150 MHz, CDCl$_3$) δ 142.9, 141.0, 140.4, 140.3, 137.8, 137.7, 137.5, 136.7, 130.9, 130.5, 130.4, 130.3, 129.2, 127.5, 127.4, 127.1, 126.6, 121.9, 121.6, 69.3, 68.7, 57.7, 57.5, 44.7, 44.4, 42.6, 33.6, 33.3, 29.0; LCMS m/z 272.1137 ([M–N$_2$+H$^+$], C$_{16}$H$_{18}$NOS requires 272.3847).

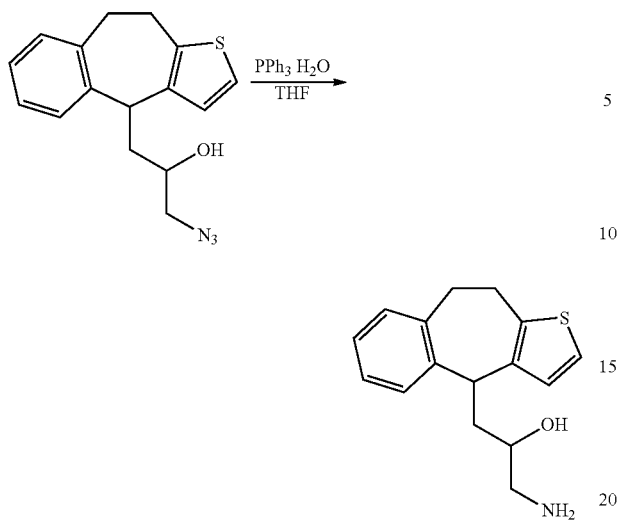

1-amino-3-(9,10-dihydro-4H-benzo[4,5]cyclohepta[1,2-b]thiophen-4-yl)propan-2-ol A solution of 1-azido-3-(9,10-dihydro-4H-benzo[4,5]cyclohepta[1,2-b]thiophen-4-yl)propan-2-ol (0.153 g, 0.511 mmol) in THF (1 mL) was cooled to 0° C., treated with PPh$_3$ (0.147 g, 0.562 mmol), H$_2$O (0.055 mL, 3.06 mmol), and stirred for 12 h at RT. The solution was concentrated to dryness, dissolved in a minimal amount of CH$_2$C$_{12}$ and purified by flash chromatography (SiO$_2$, 100% hexanes, 50% ethyl acetate-hexanes, 5%, methanol-dichloromethane, 17:2:1 dichloromethane:methanol: 35% ammonium hydroxide) to afford 1-amino-3-(9,10-dihydro-4H-benzo[4,5]cyclohepta[1,2-b]thiophen-4-yl)propan-2-ol (0.109 g, 78%). The diastereomeric ratio was determined to be 1:1.2 by $^1$H NMR analysis. $^1$H NMR (600 MHz, CDCl$_3$) δ 7.27-7.25 (1H, m), 7.22-7.14 (3H, m), 7.04-7.02 (1H, m), 1H [6.94 (d, J=5.4 Hz), 6.88 (d, J=4.8 Hz)], 1H [4.43 (dd, J=11.4, 4.2 Hz), 4.36 (dd, J=9.6, 6.0 Hz)], 3.56-3.42 (2H, m), 3.28-3.24 (1H, m), 2.99-2.91 (2H, m), 1H [2.82 (d, J=10.8 Hz), 2.69 (d, J=10.8 Hz)], 2.53-2.46 (1H, m), 2.14-0.05 (1H, m), 1.97-1.91 (4H, m); $^{13}$C NMR (150 MHz, CDCl$_3$) δ 143.6, 141.5, 140.4, 140.2, 138.5, 137.4, 137.2, 131.3, 130.6, 130.2, 129.2, 127.1, 126.9, 126.4, 121.6, 121.1, 70.0, 69.5, 47.8, 47.7, 44.7, 44.6, 43.3, 43.2, 33.6, 33.3, 29.0; LCMS m/z 274.2863 ([M+H$^+$], C$_{16}$H$_{20}$NOS requires 274.4006).

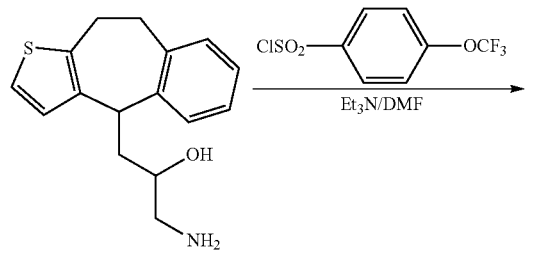

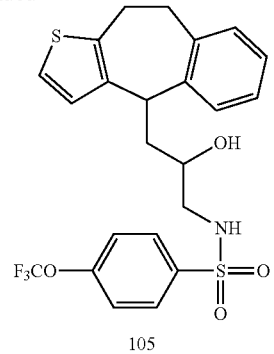

N-(3-(9,10-dihydro-4H-benzo[4,5]cyclohepta[1,2-b]thiophen-4-yl)-2-hydroxypropyl)-4-(trifluoromethoxy)benzenesulfonamide A solution 1-amino-3-(9,10-dihydro-4H-benzo[4,5]cyclohepta[1,2-b]thiophen-4-yl)propan-2-ol (0.041 g, 0.150 mmol) in DMF (1.0 mL) was cooled to 0° C., treated with Et$_3$N (0.021 mL, 0.150 mmol), and 4-(trifluoromethoxy)benzene-1-sulfonyl chloride (0.025 mL, 0.150 mmol). The mixture was warmed to RT, and stirred for 18 h. The mixture was partitioned between water (10 mL) and CH$_2$C$_{12}$ (10 mL). The organic layer was washed with saturated aqueous NaCl (30 mL×3) to remove DMF, and concentrated in vacuo. The residue was dissolved in a minimal amount of CH$_2$C$_{12}$ and purified by flash chromatography (SiO$_2$, 20%-50% ethylacetate-hexanes) to afford N-(3-(9,10-dihydro-4H-benzo[4,5]cyclohepta[1,2-b]thiophen-4-yl)-2-hydroxypropyl)-4-(trifluoromethoxy)benzenesulfonamide (105) (0.065 g, 88%). The diastereomeric ratio was determined to be 1:1.2 by $^1$H NMR analysis. $^1$H NMR (600 MHz, CD$_3$OD) δ 7.93-7.86 (2H, m), 7.42-7.37 (2H, m), 7.17-7.04 (5H, m), 1H [6.87 (d, J=4.8 Hz), 6.81 (d, J=5.4 Hz)], 1H [4.31 (dd, J=11.4, 3.6 Hz), 4.27 (d, J=9.0, 6.0 Hz)], 3.54-3.17 (4H, m), 2.93-2.78 (5H, m), 1H [2.49-2.20 (m), 2.17-2.13 (m)], 1.82-1.78 (1H, m); $^{13}$C NMR (150 MHz, CD$_3$OD) δ 151.7, 143.4, 141.2, 140.5, 140.3, 139.8, 139.7, 138.3, 137.0, 136.7, 130.6, 130.0, 129.9, 129.8, 129.0, 128.7, 126.8, 126.7, 126.4, 126.0, 121.1, 121.0, 120.8, 67.9, 67.6, 49.1, 48.7, 44.0, 43.7, 42.6, 42.4, 33.1, 32.8, 28.6; LCMS m/z 498.1076 ([M+H$^+$], C$_{23}$H$_{23}$F$_3$NO$_4$S$_2$ requires 498.5577).

Examples 106 and 107

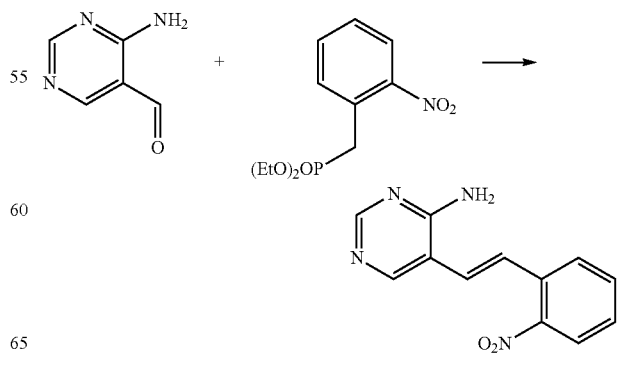

(E)-5-(2-nitrostyryl)pyrimidin-4-amine

A solution of 4-aminopyrimidine-5-carbaldehyde (1.00 g, 8.12 mmol) in DMF (10.0 mL) was treated with sodium methoxide (0.527 g, 9.75 mmol), diethyl 2-nitrobenzylphosphonate (2.22 g, 8.12 mmol) and stirred overnight at 25° C. The mixture was poured over methanol (100 mL) and the white solid that had formed was collected by filtration to afford the title compound (1.61 g, 82%). $^1$H NMR (600 MHz, DMSO-d$_6$) δ 8.40 (1H, d, J=3.6 Hz), 8.34 (1H, d, J=4.2 Hz), 8.03-8.04 (1H, m), 7.99-8.00 (1H, m), 7.75-7.77 (1H, m), 7.53-7.55 (1H, m), 7.37 (1H, dd, J=15.6, 3.6 Hz), 7.28 (1H, dd, J=16.2, 4.2 Hz), 7.16 (2H, br s); $^{13}$C NMR (150 MHz, DMSO-d$_6$) δ 160.7, 157.7, 151.9, 147.8, 133.4, 131.9, 128.7, 128.6, 125.6, 124.5, 124.3, 113.5; LCMS m/z 243.2593 ([M+H$^+$], C$_{12}$H$_{10}$N$_4$O$_2$ requires 243.2408).

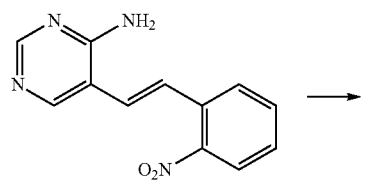

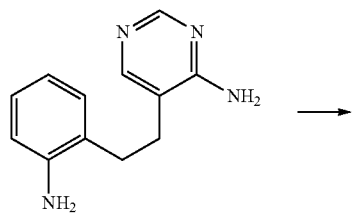

5-(2-aminophenethyl)pyrimidin-4-amine

A solution of (E)-5-(2-nitrostyryl)pyrimidin-4-amine (1.61 g, 6.65 mmol) in DMF:MeOH (1:1, 10.0 mL) was treated with 10% Pd/C (0.353 g), placed under an atmosphere of H$_2$ (g), and stirred for 14 h at 25° C. The mixture was filtered thru Celite and concentrated in vacuo. The residue was treated with H$_2$O (50 mL) and the white solid that had formed was collected by filtration to afford the title compound (1.06 g, 74%). $^1$H NMR (600 MHz, DMSO-d$_6$) δ 8.22 (1H, s), 7.90 (1H, s), 6.93 (1H, d, J=7.2 Hz), 6.89 (1H, d, J=7.2, 1.2 Hz), 6.69 (4H, br s), 6.61 (1H, d, J=7.8 Hz), 6.48 (1H, d, J=7.2 Hz), 2.65-2.68 (2H, m), 2.60-2.62 (2H, m); $^{13}$C NMR (150 MHz, DMSO-d$_6$) δ 161.8, 156.1, 153.4, 146.1, 129.0, 126.6, 124.4, 116.6, 116.1, 114.6, 28.6, 26.4; LCMS m/z 215.2180 ([M+H$^+$], C$_{12}$H$_{14}$N$_4$O requires 215.1291).

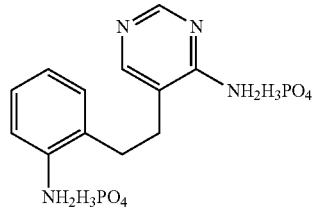

5-(2-aminophenethyl)pyrimidin-4-amine phosphoric acid salt

A solution of 5-(2-aminophenethyl)pyrimidin-4-amine (1.06 g, 4.93 mmol) in EtOH (10.0 mL) was cooled to 0° C. and treated with phosphoric acid (85%, 0.67 mL, 9.86 mmol). The solution was warmed to 25° C. and stirred for 1 h. The white solid that had formed was collected by filtration to afford the title compound as a white solid (1.91 g, 99%). $^1$H NMR (600 MHz, CD$_3$OD) δ 8.40 (1H, s), 7.76 (1H, s), 6.98 (1H, td, J=7.8, 1.8 Hz), 6.88 (1H, dd, J=7.2, 1.2 Hz), 6.74 (1H, dd, J=7.8, 0.6 Hz), 6.62 (1H, td, J=7.8, 1.2 Hz), 2.85-2.88 (2H, m), 2.80-2.83 (2H, m).

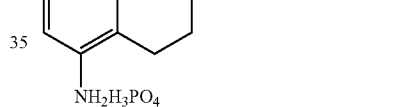

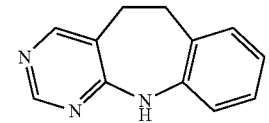

6,11-dihydro-5H-benzo[b]pyrimido[5,4-f]azepine

A suspension of 5-(2-aminophenethyl)pyrimidin-4-amine phosphoric acid salt (7.72 g, 19.5 mmol) in xylenes (20 mL) was heated to 200° C. for 2 h. The mixture was cooled to 25° C. and partitioned between saturated aqueous sodium bicarbonate (200 mL) and ethyl acetate (200 mL). The organic phase was dried (Na$_2$SO$_4$) and concentrated in vacuo. The residue was dissolved in a minimal amount of CH$_2$Cl$_2$ and purified by flash chromatography (SiO$_2$, 0-50% ethyl acetate-hexanes). The purified fractions were combined, concentrated in vacuo, suspended in a minimal amount of diethyl ether and precipitated with the addition of hexanes to afford the title compound (3.26 g, 85%) as a beige solid. $^1$H NMR (600 MHz, DMSO-d$_6$) δ 8.48 (1H, s), 8.17 (1H, s), 7.28 (1H, d, J=7.8 Hz), 7.16 (1H, t, J=7.2 Hz), 7.14 (1H, d, J=7.2 Hz), 6.91 (1H, t, J=7.2 Hz), 2.99-3.00 (2H, m), 2.88-2.90 (2H, m); $^{13}$C NMR (150 MHz, DMSO-d$_6$) δ 158.4, 156.1, 155.9, 139.3, 130.6, 130.1, 126.9, 121.7, 120.0, 118.0, 33.9, 31.0; LCMS m/z 198.1862 ([M+H$^+$], C$_{12}$H$_{11}$N$_3$ requires 198.2432).

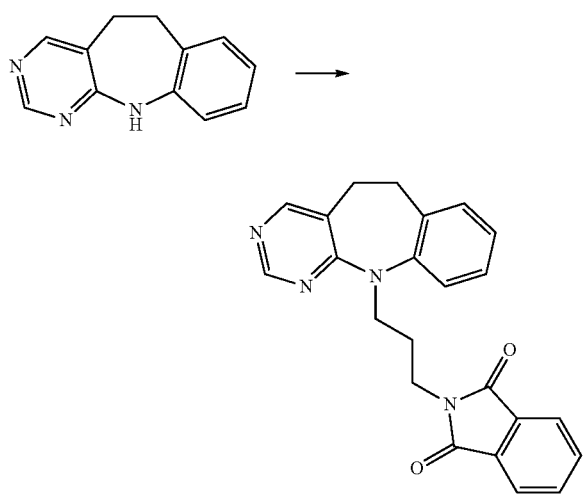 [SMILES: c1ccc2c(c1)CCc1cncnc1N2 ; O=C1c2ccccc2C(=O)N1CCCN1c2ccccc2CCc2cncnc21]

2-(3-(5H-benzo[b]pyrimido[5,4-f]azepin-11(6H)-yl) propyl)isoindoline-1,3-dione A solution of 6,11-dihydro-5H-benzo[b]pyrimido[5,4-f] azepine (1.00 g, 5.07 mmol) in DMF (10 mL) was cooled to 0° C., treated with NaH (60%, 0.304 g, 7.60 mmol), and N-(3-bromopropyl)phthalimide (2.04 g, 7.60 mmol). The solution was warmed to 25° C. and stirred for 14 h. The mixture was poured over saturated aqueous NaCl (100 mL) and extracted with $CH_2C_{12}$ (3×100 mL). The combined extracts were washed with saturated aqueous NaCl (3×100 mL), dried ($Na_2SO_4$) and concentrated in vacuo. The residue was dissolved in a minimal amount of $CH_2C_{12}$ and purified by flash chromatography ($SiO_2$, 0-75% ethyl acetate-hexanes) to afford the title compound as a brown oil (1.60 g, 82%). $^1$H NMR (600 MHz, $CDCl_3$) δ 8.45 (1H, s), 8.09 (1H, s), 7.81 (2H, dd, J=5.4, 3.0 Hz), 7.70 (2H, dd, J=5.4, 2.4 Hz), 7.21 (2H, d, J=3.6 Hz), 7.14 (1H, d, J=7.2 Hz), 7.08-7.11 (1H, m), 4.27 (2H, t, J=7.2 Hz), 3.71 (2H, t, J=7.2 Hz), 3.13-3.15 (2H, m), 2.96-2.98 (2H, m), 2.06 (2H, quintet, J=6.6 Hz); $^{13}$C NMR (150 MHz, $CDCl_3$) δ 168.5, 159.9, 157.4, 155.5, 144.6, 138.6, 134.1, 132.3, 128.7, 127.3, 125.6, 123.9, 123.4, 119.6, 48.3, 36.1, 33.7, 31.6, 27.6; LCMS m/z 385.2550 ([M+H$^+$], $C_{23}H_{20}N_4O_2$ requires 385.1659).

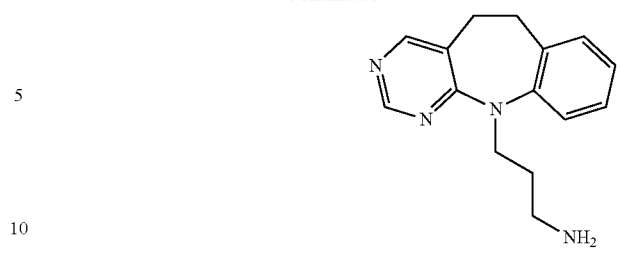

3-(5H-benzo[b]pyrimido[5,4-f]azepin-11(6H)-yl) propan-1-amine

A solution of 2-(3-(5H-benzo[b]pyrimido[5,4-f]azepin-11 (6H)-yl)propyl)isoindoline-1,3-dione (1.60 g, 4.16 mmol) in EtOH (10.0 mL) was treated with $NH_2NH_2$—$H_2O$ (0.41 mL, 8.32 mmol) and heated to 90° C. for 1 h. The mixture was cooled to 25° C., filtered and concentrated in vacuo. The residue was dissolved in a minimal amount of $CH_2C_{12}$ and purified by flash chromatography ($SiO_2$, 17:2:1 $CH_2C_{12}$: MeOH:$NH_4OH$). The purified fractions were concentrated, dried azeotropically with toluene to provide the title compound as a beige oil (0.335 g, 32%); $^1$H NMR (600 MHz, $CDCl_3$) δ 8.60 (1H, s) 8.09 (1H, s), 7.23-7.24 (2H, m), 7.14 (1H, d, J=7.2 Hz), 7.09-7.11 (1H, m), 4.27 (2H, t, J=7.2 Hz), 3.04-3.06 (2H, m), 2.95-2.97 (2H, m), 2.71 (2H, t, J=6.6 Hz), 1.79 (2H, quintet, J=6.6 Hz); $^{13}$C NMR (150 MHz, $CDCl_3$) δ 160.1, 157.3, 155.6, 144.8, 138.5, 128.5, 127.3, 125.5, 124.1, 119.5, 48.5, 40.0, 33.7, 32.4, 31.6; LCMS m/z 255.1636 ([M+H$^+$], $C_{15}H_{18}N_4$ requires 255.1604).

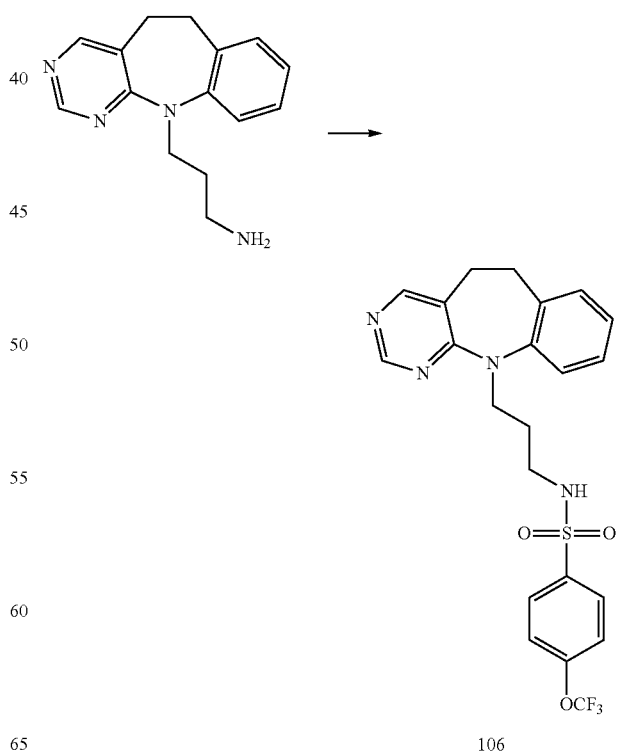

106

N-(3-(5H-benzo[b]pyrimido[5,4-f]azepin-11(6H)-yl) propyl)-4-(trifluoromethoxy)-benzenesulfonamide A solution of 3-(5H-benzo[b]pyrimido[5,4-f]azepin-11 (6H)-yl)propan-1-amine (0.068 g, 0.267 mmol) in DMF (1.0 mL) was cooled to 0° C., treated with Et$_3$N (37.0 μL, 0.267 mmol), and 4-trifluoromethoxybenzenesulfonyl chloride (45.0 μL, 0.267 mmol). The mixture was warmed to 25° C., and stirred for 2 h. The mixture was partitioned between saturated aqueous NaCl (50 mL) and CH$_2$C$_{12}$ (100 mL). The organic layer was washed with saturated aqueous NaCl (3×50 mL), dried (Na$_2$SO$_4$), and concentrated in vacuo. The residue was dissolved in a minimal amount of CH$_2$C$_{12}$ and purified by flash chromatography (SiO$_2$, 0-50% ethyl acetate-hexanes). The pure fractions were combined, concentrated, and the residue was dissolved in a minimal amount of ethyl acetate and precipitated with the addition of hexanes to afford the title compound (106) as a white solid (0.0608 g, 48%). $^1$H NMR (600 MHz, CDCl$_3$) δ 8.61 (1H, s), 8.10 (1H, s), 7.84 (2H, d, J=8.4 Hz), 7.30 (2H, d, J=8.4 Hz), 7.21-7.24 (1H, m), 7.16 (1H, d, J=7.8 Hz), 7.10-7.14 (2H, m), 5.79 (1H, t, J=5.4 Hz), 4.16 (2H, t, J=6.6 Hz), 3.01 (2H, q, J=6.6 Hz), 2.92-2.96 (4H, m), 1.92 (2H, quintet, J=6.6 Hz); $^{13}$C NMR (150 MHz, CDCl$_3$) δ 159.6, 157.5, 155.3, 152.2, 144.4, 138.5, 138.2, 129.3, 128.8, 127.5, 125.9, 123.8, 121.2, 119.7, 119.6, 48.3, 41.2, 33.8, 31.8, 28.5; LCMS m/z 479.2451 ([M+H$^+$], C$_{22}$H$_{21}$F$_3$N$_4$O$_3$S requires 479.1359).

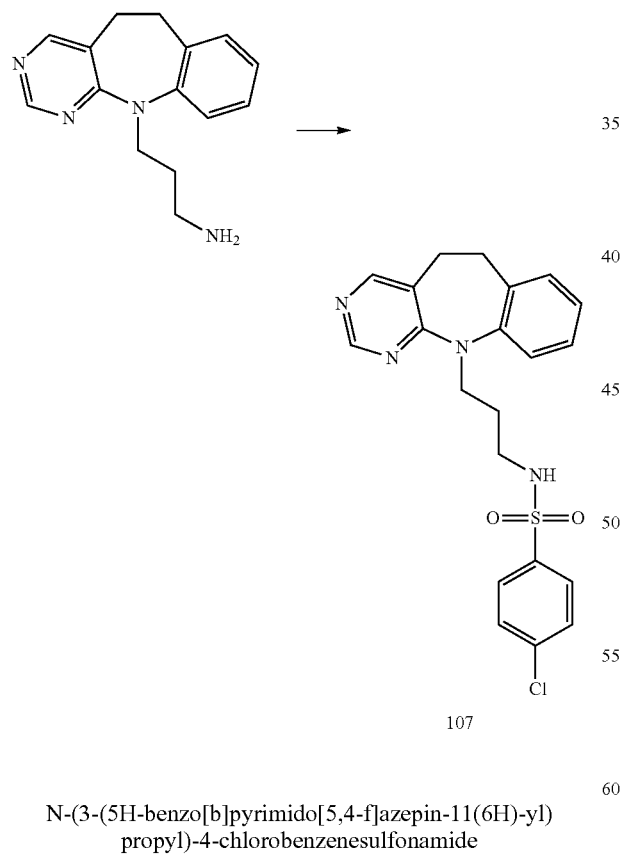

N-(3-(5H-benzo[b]pyrimido[5,4-f]azepin-11(6H)-yl) propyl)-4-chlorobenzenesulfonamide A solution of 3-(5H-benzo[b]pyrimido[5,4-f]azepin-11 (6H)-yl)propan-1-amine (0.068 g, 0.267 mmol) in DMF (1.0 mL) was cooled to 0° C., treated with Et$_3$N (37.0 μL, 0.267 mmol), and 4-chlorobenzenesulfonyl chloride (0.056 g, 0.267 mmol). The mixture was warmed to 25° C., and stirred for 2 h. The mixture was partitioned between saturated aqueous NaCl (50 mL) and CH$_2$C$_{12}$ (100 mL). The organic layer was washed with saturated aqueous NaCl (3×50 mL), dried (Na$_2$SO$_4$), and concentrated in vacuo. The residue was dissolved in a minimal amount of CH$_2$C$_{12}$ and purified by flash chromatography (SiO$_2$, 0-50% ethyl acetate-hexanes). The pure fractions were combined, concentrated, and the residue was dissolved in a minimal amount of ethyl acetate and precipitated with the addition of hexanes to afford the title compound (107) as a white solid (0.0647 g, 56%). $^1$H NMR (600 MHz, CDCl$_3$) δ 8.59 (1H, s), 8.10 (1H, s), 7.73 (2H, d, J=8.4 Hz), 7.44 (2H, d, J=8.4 Hz), 7.22 (1H, td, J=7.8, 1.8 Hz), 7.14 (1H, d, J=8.4 Hz), 7.11-7.13 (2H, m), 5.75 (1H, br s), 4.14 (2H, t, J=6.6 Hz), 3.00 (2H, q, J=6.0 Hz), 2.93 (4H, br s), 1.92 (2H, quintet, J=6.6 Hz); $^{13}$C NMR (150 MHz, CDCl$_3$) δ 159.6, 157.5, 155.3, 144.3, 139.2, 138.6, 138.2, 129.6, 128.8, 128.7, 127.5, 125.8, 123.7, 119.7, 48.1, 41.1, 33.8, 31.7, 28.4; LCMS m/z 429.1644 ([M+H$^+$], C$_{21}$H$_{21}$ClN$_4$O$_2$S requires 429.1147).

Cell Viability Assays (IC$_{50}$ Determination)

Cell viability assays were performed according to Denizot, F. and R. Lang, Journal of Immunological Methods, 1986. 89(22): p. 271-277. H1650 lung cancer cells were plated at 150,000 cells per well in a 12 well plate. Twenty-four hours after plating, cells were treated as described with increasing concentrations of drug and control. Forty-eight hours after drug treatment, cells were treated with 100 μL of 3-(4,5-Dimethylthiazol-2-yl)-2,5-diphenyltetrazolium bromide (MTT) and incubated for 2 hours at 37 C. The MTT solution was subsequently replaced with 300 μl of n-propyl alcohol and re-aliquoted to a 96 well plates. Spectrophotometric analysis of each solution was performed using a 96 well plate reader at 600 nm in triplicate. Results are shown in Table 1. The examples up to number 80 in Table 1 below are taken from PCT WO2013/025882, published 21 Feb. 2013. They illustrate biological activities of compounds that share a tricyclic scaffold.

TABLE 1

| | Cell Viability Data | |
|---|---|---|
| | Example # | IC$_{50}$ (μM) |
| 3. | N-(3-(2-chloro-10H-phenothiazin-10-yl)propyl)-4-methylbenzenesulfonamide | 20 |
| 4. | Methyl(3-(2-chloro-10H-phenothiazin-10-yl)propyl)carbamate | 10 |
| 8. | N-(3-(3-chloro-10,11-dihydro-5H-dibenzo[b,f]azepin-5-yl)propyl)-4-methylbenzenesulfonamide | 20 |
| 9. | Methyl(3-(3-chloro-10,11-dihydro-5H-dibenzo[b,f]azepin-5-yl)propyl)carbamate | 30 |
| 10. | 3-(3-(3-chloro-10,11-dihydro-5H-dibenzo[b,f]azepin-5-yl)propyl)-1,1-dimethylurea | 20 |
| 13. | N-(3-(3-chloro-10,11-dihydro-5H-dibenzo[b,f]azepin-5-yl)propyl)-3,5-difluorobenzenesulfonamide | 18 μM |
| 14. | N-(3-(2-chloro-10H-phenothiazin-10-yl)propyl)-4-cyanobenzenesulfonamide | 40 μM |
| 15. | 4-Chloro-N-(3-(2-chloro-10H-phenothiazin-10-yl)propyl)benzenesulfonamide | 20 μM |
| 17. | 3-(2-Chloro-10H-phenothiazin-10-yl)propyl)-1,1-dimethylurea | >50 |
| 18. | N-(2-(2-chloro-10H-phenothiazin-10-yl)pethyl)4-methylbenzenesulfonamide | 24.4 μM |

TABLE 1-continued

Cell Viability Data

| Example # | | IC$_{50}$ (μM) |
|---|---|---|
| 20. | N-(3-(3-chloro-10,11-dihydro-5H-dibenzo[b,f]azepin-5-yl)propyl)-4-fluorobenzenesulfonamide | >40 μM |
| 21. | N-(3-(3-chloro-10,11-dihydro-5H-dibenzo[b,f]azepin-5-yl)propyl)-4-(trifluoromethyl)benzenesulfonamide | 15.3 μM |
| 22. | N-(3-(3-chloro-10,11-dihydro-5H-dibenzo[b,f]azepin-5-yl)propyl)-4-cyanobenzenesulfonamide | 11.1 μM |
| 23. | 4-Chloro-N-(3-(3-chloro-10,11-dihydro-5H-dibenzo[b,f]azepin-5-yl)propyl)benzenesulfonamide | ~25 μM |
| 24. | N-(3-(3-chloro-10,11-dihydro-5H-dibenzo[b,f]azepin-5-yl)propyl)-4-(methylsulfonyl)benzenesulfonamide | 15.1 μM |
| 25. | N-(3-(3-chloro-10,11-dihydro-5H-dibenzo[b,f]azepin-5-yl)propyl)-4-methoxybenzenesulfonamide | <40 μM |
| 26. | 2,4-dichloro-N-(3-(3-chloro-10,11-dihydro-5H-dibenzo[b,f]azepin-5-yl)propyl)benzenesulfonamide | >40 μM |
| 27. | 4-chloro-N-(2-(2-chloro-10H-phenothiazin-10-yl)ethyl)benzenesulfonamide | 20 μM |
| 28. | N-(3-(3-chloro-10,11-dihydro-5H-dibenzo[b,f]azepin-5-yl)propyl)-4-chloro-2-fluorobenzenesulfonamide | INACTIVE |
| 29. | 3,4-dichloro-N-(3-(3-chloro-10,11-dihydro-5H-dibenzo[b,f]azepin-5-yl)propyl)benzenesulfonamide | ~25 μM |
| 30. | N-(3-(3-chloro-10,11-dihydro-5H-dibenzo[b,f]azepin-5-yl)propyl)-4-(trifluoromethoxy)benzenesulfonamide | 12.6 μM |
| 33. | 4-chloro-N-(2-(3-chloro-10,11-dihydro-5H-dibenzo[b,f]azepin-5-yl)ethyl)benzenesulfonamide | ~20 μM |
| 34. | N-(2-(3-chloro-10,11-dihydro-5H-dibenzo[b,f]azepin-5-yl)ethyl)-4-(trifluoromethyl)benzenesulfonamide | ~20 μM |
| 35. | 4-chloro-N-(3-(10,11-dihydro-5H-dibenzo[b,f]azepin-5-yl)propyl)benzenesulfonamide | ~20 μM |
| 36. | N-(3-(10,11-dihydro-5H-dibenzo[b,f]azepin-5-yl)propyl)-4-(trifluoromethyl)benzenesulfonamide | ~15 μM |
| 37. | N-(2-(3-chloro-10,11-dihydro-5H-dibenzo[b,f]azepin-5-yl)ethyl)-4-(trifluoromethoxy)benzenesulfonamide | ~25 μM |
| 38. | N-(2-(3-chloro-10,11-dihydro-5H-dibenzo[b,f]azepin-5-yl)propyl)-4-(trifluoromethoxy)benzenesulfonamide | ~10 μM |
| 39. | N-(3-(3-chloro-10,11-dihydro-5H-dibenzo[b,f]azepin-5-yl)propyl)-3-trifluoromethylbenzenesulfonamide | ~10 μM |
| 40. | N-(3-(3-chloro-10,11-dihydro-5H-dibenzo[b,f]azepin-5-yl)propyl)-4-nitrobenzenesulfonamide | ~15 μM |
| 41. | 4-trifluoromethyl-N-(2-(2-chloro-10H-phenothiazin-10-yl)ethyl)benzenesulfonamide | ~25 μM |
| 42. | 4-trifluoromethoxy-N-(2-(2-chloro-10H-phenothiazin-10-yl)ethyl)benzenesulfonamide | ~25 μM |
| 43. | N-(3-amino-10,11-dihydro-5H-dibenzo[b,f]azepin-5-yl)propyl)-4-(trifluoromethyl)benzenesulfonamide | ~35 μM |
| 44. | N-(3-azido-10,11-dihydo-5H-dibenzo[b,f]azepin-5-yl)propyl)-4-(trifluoromethyl)benzenesulfonamide | ~30 μM |
| 45. | N-(3-(3-chloro-10,11-dihydro-5H-dibenzo[b,f]azepin-5-yl)propyl)benzenesulfonamide | ~25 μM |
| 46. | N-(2-(10H-phenothiazin-10-yl)ethyl)-4-trifluoromethoxybenzenesulfonamide | ~30 μM |
| 47. | N-(2-(10H-phenothiazin-10-yl)ethyl)-4-chlorobenzenesulfonamide | ~30 μM |
| 50. | N-(3-(9H-thioxanthen-9-ylidene)propyl)-4-(trifluoromethoxy)benzenesulfonamide | ~15 μM |
| 51. | N-(3-(10,11-dihydro-5H-dibenzo[a,d][7]annulen-5-ylidene)propyl)-4-(trifluoromethoxy)benzenesulfonamide | ~20 μM |
| 52. | 4-Chloro-N-(3-(2,8-dichloro-10,11-dihydro-5H-dibenzo[b,f]azepin-5-yl)propyl)benzenesulfonamide | ~10 μM |
| 53. | 4-Trifluoromethoxy-N-(3-(2,8-dichloro-10,11-dihydro-5H-dibenzo[b,f]azepin-5-yl)propyl)benzenesulfonamide | ~10 μM |
| 54. | N-(3-(3-chloro-10,11-dihydro-5H-dibenzo[b,f]azepin-5-yl)propyl)-3-(trifluoromethoxy)benzenesulfonamide | ~15 μM |
| 55. | 4-Chloro-N-(2-((10,11-dihydro-5H-dibenzo[a,d][7]annulen-5-yl)amino)ethyl)benzenesulfonamide | ~25 μM |
| 56. | 4-Trifluoromethoxy-N-(2-((10,11-dihydro-5H-dibenzo[a,d][7]annulen-5-yl)amino)ethyl)benzenesulfonamide | ~25 μM |
| 57. | 4-Chloro-N-(3-(3-chloro-10,11-dihydro-5H-dibenzo[b,f]azepin-5-yl)-2-hydroxypropyl)benzenesulfonamide | ~10 μM |
| 58. | 4-Trifluoromethoxy-N-(3-(3-chloro-10,11-dihydro-5H-dibenzo[b,f]azepin-5-yl)-2-hydroxypropyl)benzenesulfonamide | ~5 μM |
| 59. | 4-Chloro-N-(3-(3-chloro-10,11-dihydro-5H-dibenzo[b,f]azepin-5-yl)-2-hydroxypropyl)benzenesulfonamide | ~25 μM |
| 60. | 4-Trifluoromethoxy-N-(3-(10,11-dihydro-5H-dibenzo[b,f]azepin-5-yl)-2-hydroxypropyl)benzenesulfonamide | ~15 μM |
| 61. | 4,5-dichloro-N-(3-(3-chloro-10,11-dihydro-5H-dibenzo[b,f]azepin-5-yl)propyl)thiophene-2-sulfonamide | ~20 μM |
| 62. | 2,5-dichloro-N-(3-(3-chloro-10,11-dihydro-5H-dibenzo[b,f]azepin-5-yl)propyl)thiophene-3-sulfonamide | ~25 μM |
| 63. | 5-Bromo-6-chloro-N-(3-(3-chloro-10,11-dihydro-5H-dibenzo[b,f]azepin-5-yl)propyl)pyridine-3-sulfonamide | 65% @ 20 μM |
| 64. | N-(3-(10,11-dihydro-5H-dibenzo[b,f]azepin-5-yl)-2-oxopropyl)-4-(trifluoromethoxy)benzenesulfonamide | ~35 μM |
| 65. | N-(2-cyano-3-(10,11-dihydro-5H-dibenzo[b,f]azepin-5-yl)propyl)-4-(trifluoromethoxy)benzenesulfonamide | ~15 μM |
| 66. | N-(3-(10,11-dihydro-5H-dibenzo[b,f]azepin-5-yl)propyl)pyridine-3-sulfonamide | N/A |
| 67. | N-(3-(10,11-dihydro-5H-dibenzo[b,f]azepin-5-yl)-2-methylpropyl)-4-(trifluoromethoxy)benzenesulfonamide | ~20 μM |
| 68. | 4-Chloro-N-(3-(10,11-dihydro-5H-dibenzo[b,f]azepin-5-yl)-2-methylpropyl)benzenesulfonamide | ~20 μM |
| 69. | N-(3-(4-chloro-10,11-dihydro-5H-dibenzo[b,f]azepin-5-yl)propyl)-4-(trifluoromethoxy)benzenesulfonamide | ~20 μM |
| 70. | 4-Chloro-N-(3-(4-chloro-10,11-dihydro-5H-dibenzo[b,f]azepin-5-yl)propyl)benzenesulfonamide | ~20 μM |
| 71. | N-(3-(10,11-dihydro-5H-dibenzo[a,d][7]annulen-5-ylidene)propyl)-4-cyanobenzenesulfonamide | 25 |

TABLE 1-continued

Cell Viability Data

| Example # | | IC$_{50}$ (μM) |
|---|---|---|
| 72. | N-(3-(10,11-dihydro-5H-dibenzo[a,d][7]annulen-5-ylidene)propyl)-4-fluorobenzenesulfonamide | 20 |
| 73. | trans-N-(3-(10,11-dihydro-5H-dibenzo[b,f]azepin-5-yl)cyclohexyl)-4-(trifluoromethoxy)benzenesulfonamide | 15 |
| 73. | cis-N-(3-(10,11-dihydro-5H-dibenzo[b,f]azepin-5-yl)cyclohexyl)-4-(trifluoromethoxy)benzenesulfonamide | 5 |
| 74. | (S)-N-(3-(10,11-dihydro-5H-dibenzo[b,f]azepin-5-yl)-2-hydroxypropyl)-4-(trifluoromethoxy)benzenesulfonamide | ~15 μM |
| 75. | (R)-N-(3-(10,11-dihydro-5H-dibenzo[b,f]azepin-5-yl)-2-hydroxypropyl)-4-(trifluoromethoxy)benzenesulfonamide | ~15 μM |
| 76. | N-(3-(10,11-dihydro-5H-dibenzo[b,f]azepin-5-yl)cyclopentyl)-4-(trifluoromethoxy)benzenesulfonamide | 20 |
| 77. | N-(3-(10,11-dihydro-5H-dibenzo[a,d][7]annulen-5-ylidene)cyclohexyl)-4-(trifluoromethoxy)benzenesulfonamide | 15 |
| 78. | N-(3-(10,11-dihydro-5H-dibenzo[a,d][7]annulen-5-ylidene)cyclohexyl)-4-chlorobenzenesulfonamide | 15 |
| 79. | N-(4-(10,11-dihydro-5H-dibenzo[a,d][7]annulen-5-ylidene)cyclohexyl)-4-(trifluoromethoxy)benzenesulfonamide | ~20 |
| 80. | N-(4-(10,11-dihydro-5H-dibenzo[a,d][7]annulen-5-ylidene)cyclohexyl)-4-chlorobenzenesulfonamide | ~20 |
| 100 | | 20 μM |
| 101 | | 25 μM |
| 102 | | 30 μM |
| 103 | | 30 μM |

Colony Formation Assay. The protocol follows Sangodkar et al. J Clin Invest 2012; 122:2637-51.

Cell culture and staining: For both A549luc and H292 cells, 500 cells were seeded into each well of a 6-well plate and allowed to attach for 24 hours before drug treatment. The following day, cells were treated with either the appropriate dose of drug or an equivalent volume of DMSO (two replicates were treated for each condition). For each condition, depleted media was replaced with fresh media containing the equivalent drug dose four days after initial treatment. Cells were harvested either 7 (A549luc) or 8 (H292) days after initial treatment. Briefly, media was aspirated from each well and the cells were washed twice with ice-cold PBS, then plates were allowed to dry at room temperature for 4 hours. Cells were fixed for one hour in a fixing solution consisting of 10% methanol and 10% glacial acetic acid in distilled water, then stained overnight in 1% (w/v) crystal violet dissolved in methanol. The next day, staining solution was aspirated from the wells and plates were washed gently with distilled water to remove excess stain before colony counting. Colonies were imaged on a ChemiDoc XRS+(Bio-Rad) and images were exported as 8-bit TIFF files. Colonies were counted using the Colony Counter plugin in ImageJ, with colony size defined as between 4 and 400 square pixels, and minimum circularity set at 0.6. Duplicate wells were averaged to obtain a single value for each condition. Results (number of colonies) for A549luc cells are shown in Table 2 and results (number of colonies) for H292 cells are shown in Table 3:

TABLE 2

| Example # | 5 μM | 7.5 μM | 10 μM |
|---|---|---|---|
| DMSO blank | 146 | 159 | 161.5 |
| 30 | 116 | 111.5 | 67.5 |
| 60 | 126.5 | 118.5 | 56 |
| 74 | 135.5 | 118.5 | 96 |
| 75 | 133.5 | 105 | 63.5 |
| 73 | 2 | 0 | 0 |

TABLE 3

| Example # | 5 μM | 7.5 μM | 10 μM |
|---|---|---|---|
| DMSO blank | 111 | 108 | 120 |
| 30 | 95 | 74.5 | 61 |
| 60 | 107 | 105 | 42 |
| 74 | 85.5 | 65.5 | 46.5 |
| 75 | 109.5 | 80 | 47 |
| 73 | 40.5 | 16.5 | 7 |

In Vivo Cancer Model

The in vivo lung cancer model is described in Politi et al., Genes Dev. Jun. 1, 2006 20: 1496-1510. EGFR-L858R/CCSP mice were fed doxycycline-impregnanted food pellets to induce tumor formation. After 8-12 weeks, mice were imaged in a Bruker 4.7T Biospec scanner to confirm lung nodule development. After tumor confirmation, the compound of Example 30 was prepared in DMSO (Sigma) and administered i.p. at 100 mg/kg every other day for two weeks. After treatment, the mice were re-imaged by MRI, and pre-treatment and post-treatment lung volumes were calculated by visible lung opacity present in each axial image using Osirix 4.1.1. DMSO control animals show a 20% increase in tumor volume over two week treatment period. Animals treated with the compound of Example 30 show a 60% decrease in tumor volume over two week treatment period.

As mentioned above, CD4+ Foxp3+ regulatory T cells (Tregs) are required for self-tolerance and are essential for induction of allograft tolerance in animals. Immunosuppressive medications required for treating autoimmunity and preventing transplant rejection, including calcineurin inhibitors, nonspecifically inhibit all T cells including Treg. Such pharmacological inhibition of Treg prevents, rather than promotes, allograft tolerance, subjecting the individual to the toxicities of long term immunosuppression, including an increased risk of developing malignancy because anti-tumor immune surveillance is blocked. Thus, immunosuppressants capable of facilitating Treg induction and function, and simultaneously preventing malignancy could be transformative in the care of patients with immune mediated diseases, including transplant rejection.

Example 30 has been tested for its ability to induce Treg from naïve CD4 T cells. These experiments revealed that Example 30 facilitated upregulation of Foxp3 in naïve polyclonal treated with TGFβ and TCR transgenic T cells stimulated in vivo during costimulatory blockade, and the induced Tregs functionally suppressed alloreactive T cells in a suppression assay. Fifty thousand CD4 naïve cells (CD62Lhi,CD25 low, CD4 positive) were incubated with 2 ng/mL TGFβ, 1 ug/mL anti-CD3, 100 ng/mL IL-2, 50000 APCs per well and the compounds 10 μM, 5 μM and 2.5 μM concentrations. The cells were incubated for 3 days and then stained for CD4 and Foxp3 expression. Results were expressed as fold increase over the % induced in control (DMSO) wells (typically 20-25% Foxp3+). AKTi, a small molecule AKT inhibitor, was used as a positive control; it induced about a 4-fold increase. Haloperidol was used as a specificity control; it did not induce a statistically significant increase. Example 30 exhibited a greater than 2 fold increase in iTreg at 2.5 µM. Example 27 exhibited a 2 fold increase in iTreg at 5 µM. The effects of Example 30 on iTreg induction are amplified as the TGFβ concentration decreases. Results of suppression assays using iTreg induced with or without Example 30 demonstrate equivalent suppressive capacity, presented as % inhibition of maximal proliferation induced in the absence of Treg.

To test for a clinically relevant in vivo effect, BALB/c hearts were transplanted into fully allogeneic B6 recipients. While untreated animals rejected their grafts by day 8 n=4, the grafts in the mice treated with 100 mg/kg i.p. of Example 30 lasted 18 days n=4, p<0.05 vs control, a statistically and clinically significant effect.

The invention claimed is:
1. A compound of formula (I):

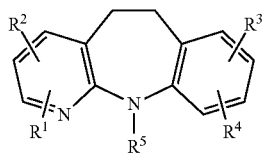

I $R^1$, $R^2$, $R^3$, and $R^4$ are independently selected from the group consisting of: H, halo, $-N_3$, $-NR^6R^7$, $(C_1-C_6)$alkyl, $(C_1-C_6)$haloalkyl, $-OR^6$, $-C(O)R^6$, $-OC(O)R^6$, $-C(O)NR^6R^7$, $-C(O)OR^6$, $-SR^6$, $-SO_2R^6$, and $-SO_2NR^6R^7$;

$R^5$ is $-(CR^{15}R^{16})_p-Q_q-(CR^{15}R^{16})_{n-p}-Z$ or

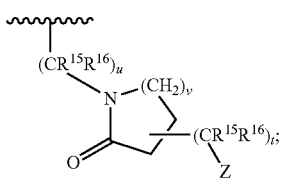

Q is chosen from $-O-$, $-NR^{14}-$ and

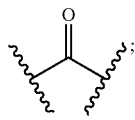

each $R^6$ and $R^7$ is independently selected from the group consisting of: H and $(C_1-C_6)$alkyl;
$R^{14}$ is H or $(C_1-C_3)$alkyl;
$R^{15}$ and $R^{16}$, in each occurrence are chosen independently from H, OH, cyano, amino, $(C_1-C_3)$alkylamino, $(C_1-C_3)$dialkylamino, $(C_1-C_3)$alkyl, $(C_1-C_3)$haloalkyl, $(C_1-C_3)$haloalkoxy, and $(C_1-C_3)$alkoxy, or, taken together, two of $R^{15}$ and $R^{16}$ may form a three to seven membered heterocycle or non-aromatic carbocycle, wherein said three to seven membered carbocycle or hetero-cycle may be additionally substituted with one or two substituents chosen from OH, F, cyano, amino, $(C_1-C_3)$alkylamino, $(C_1-C_3)$dialkylamino, $(C_1-C_3)$alkyl, $(C_1-C_3)$haloalkyl, $(C_1-C_3)$haloalkoxy, and $(C_1-C_3)$alkoxy;

n is an integer from 2 to 4;

p is zero, 1 or 2;

q is zero or 1;

t is zero, 1 or 2;

u is zero, 1 or 2, that when Y is

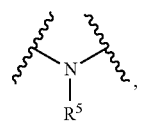

is 2;

v is 1, 2 or 3;

Z is selected from the group consisting of: $-NHSO_2R^{17}$, $-NHC(O)NR^8R^9$, $-NHC(O)OR^8$, $-S(O)_2NR^8R^9$, substituted or unsubstituted cyclic carbamate; substituted or unsubstituted cyclic urea, cyclic imide and cyanoguanidine;

$R^8$ and $R^9$ are independently selected from H, substituted or unsubstituted $(C_1-C_6)$alkyl, substituted or unsubstituted $(C_3-C_7)$ cycloalkyl and substituted or unsubstituted $(C_5-C_{14})$aryl; and $R^{17}$ is chosen from phenyl and monocyclic heteroaryl, said phenyl and monocyclic heteroaryl optionally substituted with one or two substituents chosen from OH, halogen, cyano, nitro, $(C_1-C_3)$alkylamino, $(C_1-C_3)$dialkylamino, $(C_1-C_3)$acylamino, $(C_1-C_3)$alkylsulfonyl, $(C_1-C_3)$alkylthio, $(C_1-C_3)$alkyl, $(C_1-C_3)$haloalkyl, $(C_1-C_3)$haloalkoxy, and $(C_1-C_3)$alkoxy.

2. A compound according to claim 1, wherein Z is selected from the group consisting of: $-NHSO_2R^7$, $-NHC(O)NR^8R^9$, and $-NHC(O)OR^8$.

3. A compound according to claim 2 wherein Z is $-NHSO_2R^{17}$.

4. A compound according to claim of formula:

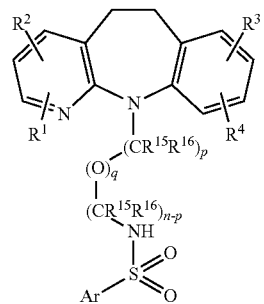

wherein Ar is a substituted or unsubstituted phenyl, thienyl, furanyl or pyrrolyl.

5. A compound according to claim 4 wherein p and q are both zero, $R^1$ is H and $R^{16}$ is chosen from H and OH.

6. A compound according to claim 5 of formula:

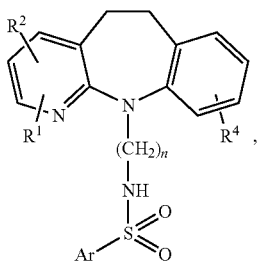

ID

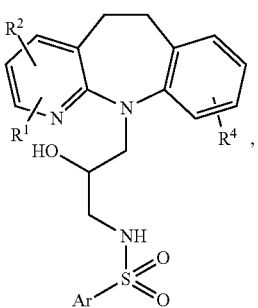

ID' wherein:
R$^1$ is independently selected from the group consisting of: H and halo; and
R$^2$ and R$^4$ are H.

7. A compound according to claim 4 wherein two R$^{15}$ or R$^{16}$ taken together form a three to seven membered carbocycle or heterocycle B, wherein said three to seven membered carbocycle or heterocycle B may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy, said compound being of formula:

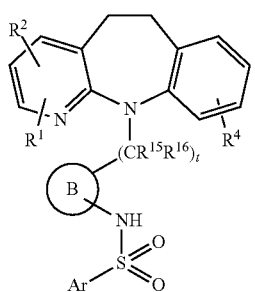

wherein
t is zero, 1 or 2; and
Ar is a substituted or unsubstituted phenyl, thienyl, furanyl or pyrrolyl.

8. A compound according to claim 7 wherein
(a) B is a five-membered ring of formula:

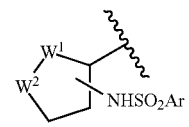

wherein, in the five-membered ring:
W$^1$ and W$^2$ are both —CH$_2$—; or
one of W$^1$ and W$^2$ is —O— and the other is —CH$_2$—; or
one of W$^1$ and W$^2$ is —CH(OH)— and the other is —CH$_2$— and the arylsulfonamide replaces one hydrogen on one CH$_2$ group; or
(b) B is a six-membered ring of formula:

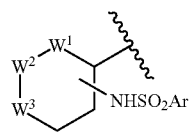

wherein, in the six-membered ring:
all of W$^1$W$^2$ and W$^3$ are —CH$_2$—; or
one of W$^1$W$^2$ and W$^3$ is —O— and the other two are —CH$_2$—; or
one of W$^1$W$^2$ and W$^3$ is —CH(OH)— and the other two are —CH$_2$—
and the arylsulfonamide replaces one hydrogen on one CH$_2$ group.

9. A compound according to claim 4 wherein two R$^{15}$ or R$^{16}$ taken together form a three to seven membered carbocycle or heterocycle B, wherein said three to seven membered carbocycle or heterocycle B may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy, said compound being of formula:

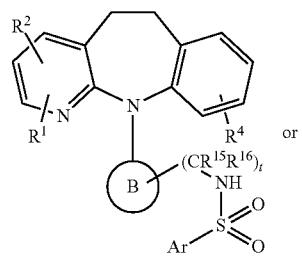

wherein
t is zero, 1 or 2; and
Ar is a substituted or unsubstituted phenyl, thienyl, furanyl or pyrrolyl.

10. A compound according to claim 9, wherein
(a) B is a five-membered ring of formula:

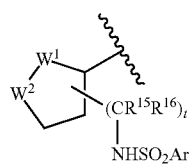

wherein, in the five-membered ring:
W$^1$ and W$^2$ are both —CH$_2$—; or
one of W$^1$ and W$^2$ is —O— and the other is —CH$_2$—; or
one of W$^1$ and W$^2$ is —CH(OH)— and the other is —CH$_2$— and the arylsulfonamide replaces one hydrogen on one CH$_2$ group; or (b) B is a six-membered ring of formula:

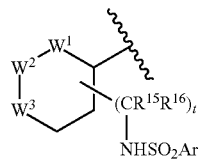

wherein, in the six-membered ring:
all of W$^1$W$^2$ and W$^3$ are —CH$_2$—; or
one of W$^1$W$^2$ and W$^3$ is —O— and the other two are —CH$_2$—; or
one of W$^1$W$^2$ and W$^3$ is —CH(OH)— and the other two are —CH$_2$— and the arylsulfonamide replaces one hydrogen on one CH$_2$ group.

11. A compound according to claim 4 wherein Ar is phenyl or thienyl, optionally substituted with one or two substituents chosen from (C$_1$-C$_3$)alkyl, halogen, cyano, nitro, (C$_1$-C$_3$)haloalkyl, (C$_1$-C$_3$)alkylsulfonyl, (C$_1$-C$_3$)haloalkoxy, and acetylamino.

12. A compound according to claim 1 wherein t is zero.

13. A compound according to claim 4 wherein
Ar is phenyl, optionally substituted at the 3, 4 or 5 positions with one or two substituents chosen from methyl, halogen, cyano, trifluoromethyl and trifluoromethoxy;
R$^1$ and R$^3$ are independently selected from the group consisting of H and halo; and
R$^2$ and R$^4$ are H.

14. A pharmaceutical composition comprising a pharmaceutically acceptable carrier and a compound according to claim 1.

* * * * *

UNITED STATES PATENT AND TRADEMARK OFFICE
CERTIFICATE OF CORRECTION

| | |
|---|---|
| PATENT NO. | : 9,796,717 B2 |
| APPLICATION NO. | : 14/768632 |
| DATED | : October 24, 2017 |
| INVENTOR(S) | : Ohlmeyer et al. |

It is certified that error appears in the above-identified patent and that said Letters Patent is hereby corrected as shown below:

In the Claims

Column 54, Line 12: Claim 1, Delete "us is zero, 1 or 2, that when Y is 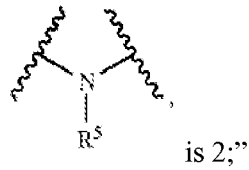 is 2;"

and insert -- "us is zero, 1 or 2, that when Y is 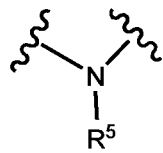 , u is 2; --

Column 54, Line 46: Claim 4, Delete "according to claim of formula:" and insert -- according to claim 3 of formula: --

Column 54, Line 67: Claim 5, Delete "$R^1$ is H" and insert -- $R^{15}$ is H --

Column 55, Line 15: Claim 6, Insert -- or --

Signed and Sealed this
Twenty-fourth Day of April, 2018

Andrei Iancu
*Director of the United States Patent and Trademark Office*